US011365391B2

(12) United States Patent
Sentman et al.

(10) Patent No.: US 11,365,391 B2
(45) Date of Patent: Jun. 21, 2022

(54) CHIMERIC ANTIGEN RECEPTOR ANTI-INFLAMMATORY CELLS AND METHODS OF USE

(71) Applicant: TRUSTEES OF DARTMOUTH COLLEGE, Hanover, NH (US)

(72) Inventors: Charles L. Sentman, Grantham, NH (US); Benjamine H. Arellano, Lebanon, NH (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 134 days.

(21) Appl. No.: 15/762,723

(22) PCT Filed: Sep. 27, 2016

(86) PCT No.: PCT/US2016/053893
§ 371 (c)(1),
(2) Date: Mar. 23, 2018

(87) PCT Pub. No.: WO2017/058752
PCT Pub. Date: Apr. 6, 2017

(65) Prior Publication Data
US 2018/0265846 A1    Sep. 20, 2018

Related U.S. Application Data

(60) Provisional application No. 62/233,517, filed on Sep. 28, 2015.

(51) Int. Cl.
*A61K 35/17* (2015.01)
*A61K 48/00* (2006.01)
*C12N 5/0783* (2010.01)
*A61K 38/17* (2006.01)
*C07K 14/705* (2006.01)
*C07K 14/47* (2006.01)
*C07K 14/54* (2006.01)
*C07K 16/18* (2006.01)

(52) U.S. Cl.
CPC ............ *C12N 5/0637* (2013.01); *A61K 35/17* (2013.01); *A61K 38/178* (2013.01); *C07K 14/4702* (2013.01); *C07K 14/5428* (2013.01); *C07K 14/7056* (2013.01); *C07K 14/70503* (2013.01); *C07K 16/18* (2013.01); *A61K 48/00* (2013.01); *C07K 2317/622* (2013.01); *C07K 2319/00* (2013.01); *C12N 2510/00* (2013.01)

(58) Field of Classification Search
CPC ...... A61K 35/17; A61K 38/178; A61K 48/00; C07K 14/4702; C07K 14/7056; C07K 14/70503; C12N 5/0637; C12N 2510/00
See application file for complete search history.

(56) References Cited

U.S. PATENT DOCUMENTS

| 4,690,915 | A | 9/1987 | Rosenberg |
| 4,694,778 | A | 9/1987 | Learn et al. |
| 6,106,823 | A * | 8/2000 | Vieira ................ A61K 38/2026 424/85.2 |
| 6,410,319 | B1 | 6/2002 | Raubitschek et al. |
| 7,994,298 | B2 * | 8/2011 | Zhang .................. C07K 14/715 536/23.1 |
| 8,192,984 | B2 | 6/2012 | Atabekov et al. |
| 2002/0119571 | A1 * | 8/2002 | Ritter .................... A61K 39/001 435/456 |
| 2005/0112095 | A1 | 5/2005 | Hsu et al. |
| 2006/0024333 | A1 * | 2/2006 | O'Connor .............. A61K 35/62 424/265.1 |
| 2010/0135974 | A1 | 6/2010 | Eshhar et al. ............. 424/93.71 |
| 2010/0303721 | A1 * | 12/2010 | Weinstock ............. A61K 35/62 424/9.1 |
| 2012/0029063 | A1 | 2/2012 | Zhang et al. ................ 514/44 R |
| 2014/0255363 | A1 * | 9/2014 | Metelitsa ............... A61K 39/00 424/93.21 |
| 2014/0370017 | A1 | 12/2014 | June et al. .................. 424/135.1 |
| 2015/0038684 | A1 | 2/2015 | Jensen ........................ 530/391.9 |
| 2016/0045581 | A1 * | 2/2016 | Ince ................. G01N 33/56972 424/265.1 |

FOREIGN PATENT DOCUMENTS

WO    WO 2010/119257    10/2010

OTHER PUBLICATIONS

Jethwa et al, Clin. Immunol. 150: 51-63, 2014; available online Nov. 16, 2013.*
Fransson et al, J. Neuroinflamm. 9:112, 12 pages, 2012.*
Bluestone et al, Expert Op. Therapeutic Targets 19(8): 1091-1103, Apr. 16, 2015.*
Andolfi et al, Mol. Therapy 20(9): 1778-1790, 2012.*
Lu et al, J. Leukoc. Biol. 66: 293-296, 1999.*
Chmielewski et al, Cancer Res. 71(17): 5697-5706, 2011.*
Chen et al, Blood 107(4): 1459-1467, 2006.*

(Continued)

*Primary Examiner* — Kevin K Hill
(74) *Attorney, Agent, or Firm* — Robin L. Teskin; Baker, Donelson, Bearman, Caldwell & Berkowitz PC

(57) ABSTRACT

A nucleic acid construct and an immune cell, which harbor nucleic acids encoding a CAR and nucleic acids encoding at least one anti-inflammatory or immunosuppressant protein and methods of using the same in treatment or amelioration of inflammation or immune-mediated autoimmunity are described.

22 Claims, 1 Drawing Sheet
Specification includes a Sequence Listing.

(56) References Cited

OTHER PUBLICATIONS

Dobson et al, In the Light of Evolution: vol. II: Biodiversity and Extinction, Washington (DC): National Academies Press (US); 2008. 4, Homage to Linnaeus: How Many Parasites? How Many Hosts? Available from: https://www.ncbi.nlm.nih.gov/books/NBK214895/ ; pp. 63-82, 2008; abstract only.*
Zelensky et al, FEBS J. 6179-6217, 2005.*
Ditgen et al. "Harnessing the Helminth Secretome for Therapeutic Immunomodulators" BioMed Research International 2014 vol. 2014 Article ID 964350 1-14.
Kerkar, S.P. "'Model T' cells: a time-tested vehicle for gene therapy" Frontiers in Immunology 2103 4(304):1-7.
Lucas A. & McFadden, G. "Secreted Immunomodulatory Viral Proteins as Novel Biotherapeutics" J. Immunol. 2004 173:4765-4774.
Mathisen et al. "Treatment of Experimental Autoimmune Encephalomyelitis with Genetically Modified Memory T Cells" J. Exp. Med. 1997 186(1):159-164.
International Search Report and Written Opinion in PCT/US16/53893 dated Dec. 9, 2016.
International Preliminary Report on Patentability in PCT/US16/53893 dated Apr. 12, 2018.
Allen JB, et al. "Suppression of monocyte function and differential regulation of IL-1 and IL-1ra by IL-4 contribute to resolution of experimental arthritis," J Immunol. Oct. 15, 1993;151(8):4344-51.
Altenschmidt U, et al. "Cytolysis of tumor cells expressing the Neu/erbB-2, erbB-3, and erbB-4 receptors by genetically targeted naive T lymphocytes," Clin Cancer Res. Jun. 1996;2(6):1001-8.
Andus T, et al. "Imbalance of the interleukin 1 system in colonic mucosa-association with intestinal inflammation and interleukin 1 receptor antagonist [corrected] genotype 2," Gut. Nov. 1997;41(5):651-7.
Arend WP, et al. "Effects of immune complexes on production by human monocytes of interleukin 1 or an interleukin 1 inhibitor," J Immunol. Jun. 1985;134(6):3868-75.
Arend WP. "Interleukin-1 receptor antagonist," Adv Immunol. 1993;54:167-227.
Arondel J, et al. "Increased interleukin-1 (IL-1) and imbalance between IL-1 and IL-1 receptor antagonist during acute inflammation in experimental Shigellosis," Infect Immun. Nov. 1999;67(11):6056-66.
Asadullah K, et al. "IL-10 is a key cytokine in psoriasis. Proof of principle by IL-10 therapy: a new therapeutic approach," J Clin Invest. Feb. 15, 1998;101(4):783-94.
Awasthi A, et al. "A dominant function for interleukin 27 in generating interleukin 10-producing anti-inflammatory T cells," Nat Immunol. Dec. 2007;8(12):1380-9. Epub Nov. 11, 2007.
Ayroldi E, et al. "Glucocorticoid-induced leucine zipper (GILZ): a new important mediator of glucocorticoid action," FASEB J. Nov. 2009;23(11):3649-58.
Balic A, et al. "Selective maturation of dendritic cells by Nippostrongylus brasiliensis-secreted proteins drives Th2 immune responses," Eur J Immunol. Nov. 2004;34(11):3047-59.
Barthel R, et al. "T cell-specific expression of the human TNF-alpha gene involves a functional and highly conserved chromatin signature in intron 3," J Immunol. Oct. 1. 2003;171(7):3612-9.
Batten M, et al. "Interleukin 27 limits autoimmune encephalomyelitis by suppressing the development of interleukin 17-producing T cells," Nat Immunol. Sep. 2006;7(9):929-36.
Baumhofer JM, et al. "Gene transfer with IL-4 and IL-13 improves survival in lethal endotoxemia in the mouse and ameliorates peritoneal macrophages immune competence," Eur J Immunol. Feb. 1998;28(2):610-5.
Beatty GL, et al. "Mesothelin-specific chimeric antigen receptor mRNA-engineered T cells induce antitumor activity in solid malignancies," Cancer Immunol Res. Feb. 2014;2(2):112-20.

Berkman N, et al. "Inhibition of inducible nitric oxide synthase expression by interleukin-4 and interleukin-13 in human lung epithelial cells," Immunology. Nov. 1996;89(3):363-7.
Bhatia M, et al. "Pathophysiology of acute pancreatitis," Pancreatology. 2005;5(2-3):132-44.
Bird RE, et al. "Single-chain antigen-binding proteins," Science. Oct. 21, 1988;242(4877):423-6.
Bochner BS, et al. "IL-13 selectively induces vascular cell adhesion molecule-1 expression in human endothelial cells," J Immunol. Jan. 15, 1995;154(2):799-803.
Bonini C, et al. "HSV-TK gene transfer into donor lymphocytes for control of allogeneic graft-versus-leukemia," Science. Jun. 13, 1997;276(5319):1719-24.
Bresnihan B. "Anakinra as a new therapeutic option in rheumatoid arthritis: clinical results and perspectives," Clin Exp Rheumatol. Sep.-Oct. 2002;20(5 Suppl 27):S32-4.
Canevari S, et al. "Regression of advanced ovarian carcinoma by intraperitoneal treatment with autologous T lymphocytes retargeted by a bispecific monoclonal antibody," J Natl Cancer Inst. Oct. 4, 1995;87(19):1463-9.
Caron JP, et al. "Chondroprotective effect of intraarticular injections of interleukin-1 receptor antagonist in experimental osteoarthritis. Suppression of collagenase-1 expression," Arthritis Rheum. Sep. 1996;39(9):1535-44.
Carpenito C, et al. "Control of large, established tumor xenografts with genetically retargeted human T cells containing CD28 and CD137 domains," Proc Natl Acad Sci U S A. Mar. 3, 2009;106(9):3360-5.
Casini-Raggi V, et. al. "Mucosal imbalance of IL-1 and IL-1 receptor antagonist in inflammatory bowel disease. A novel mechanism of chronic intestinal inflammation," J Immunol. Mar. 1, 1995;154(5):2434-40.
Chen H, et al. "Viral serpin therapeutics from concept to clinic," Methods Enzymol. 2011;499:301-29.
Chmielewski M, et al. "T cell activation by antibody-like immunoreceptors: increase in affinity of the single-chain fragment domain above threshold does not increase T cell activation against antigen-positive target cells but decreases selectivity," J Immunol. Dec. 15, 2004;173(12):7647-53.
Colamonici OR, et al. "Vaccinia virus B18R gene encodes a type I interferon-binding protein that blocks interferon alpha transmembrane signaling," J Biol Chem. Jul. 7, 1995;270(27):15974-8.
Colgan J, et al. "All in the family: IL-27 suppression of T(H)-17 cells," Nat Immunol. Sep. 2006;7(9):899-901.
Collison LW, et al. "Interleukin-35: odd one out or part of the family?" Immunol Rev. Dec. 2008;226:248-62.
Collison LW, et al. "The inhibitory cytokine IL-35 contributes to regulatory T-cell function," Nature. Nov. 22, 2007;450(7169):566-9.
Dai H, et al. "Interleukin-10 plays a crucial role in suppression of experimental autoimmune encephalomyelitis by Bowman-Birk inhibitor," J Neuroimmunol. Apr. 2012;245(1-2):1-7.
Davies DM, et al. "Flexible targeting of ErbB dimers that drive tumorigenesis by using genetically engineered T cells," Mol Med. May 9, 2012;18:565-76.
De Waal Malefyt et al. "Effects of IL-13 on phenotype, cytokine production, and cytotoxic function of human monocytes. Comparison with IL-4 and modulation by IFN-gamma or IL-10." The Journal of Immunology. Dec. 1, 1993;151(11):6370-81.
De Waal Malefyt R, et al. "Interleukin 10 (IL-10) and viral IL-10 strongly reduce antigen-specific human T cell proliferation by diminishing the antigen-presenting capacity of monocytes via downregulation of class II major histocompatibility complex expression," J Exp Med. Oct. 1, 1991;174(4):915-24.
De Waal Malefyt R, et al. "Interleukin 10(IL-10) inhibits cytokine synthesis by human monocytes: an autoregulatory role of IL-10 produced by monocytes," J Exp Med. Nov. 1, 1991;174(5):1209-20.
Devergne O, et al. "Epstein-Barr virus-induced gene 3 and the p35 subunit of interleukin 12 form a novel heterodimeric hematopoietin," Proc Natl Acad Sci U S A. Oct. 28, 1997;94(22):12041-6.
Di Santo E, et al. "IL-13 inhibits TNF production but potentiates that of IL-6 in vivo and ex vivo in mice," J Immunol. Jul. 1, 1997;159(1):379-82.

(56) References Cited

OTHER PUBLICATIONS

Dripps DJ, et al. "Interleukin-1 (IL-1) receptor antagonist binds to the 80-kDa IL-1 receptor but does not initiate IL-1 signal transduction," J Biol Chem. Jun. 5, 1991;266(16):10331-6.
Dubois CM, et al. "Transforming growth factor beta is a potent inhibitor of interleukin 1 (IL-1) receptor expression: proposed mechanism of inhibition of IL-1 action," J Exp Med. Sep. 1, 1990;172(3):737-44.
Duval L, et al. "Adoptive transfer of allogeneic cytotoxic T lymphocytes equipped with a HLA-A2 restricted MART-1 T-cell receptor: a phase 1 trial in metastatic melanoma," Clin Cancer Res. Feb. 15, 2006;12(4):1229-36.
Essner R, et al. "IL-4 down-regulates IL-1 and TNF gene expression in human monocytes," J Immunol. Jun. 1, 1989;142(11):3857-61.
Fitzgerald DC, et al. "Suppression of autoimmune inflammation of the central nervous system by interleukin 10 secreted by interleukin 27-stimulated T cells," Nat Immunol. Dec. 2007;8(12):1372-9.
Fitzgerald DC, et al. "Suppressive effect of IL-27 on encephalitogenic Th17 cells and the effector phase of experimental autoimmune encephalomyelitis," J Immunol. Sep. 1, 2007;179(5):3268-75.
Geiser AG, et al. "Transforming growth factor beta 1 (TGF-beta 1) controls expression of major histocompatibility genes in the postnatal mouse: aberrant histocompatibility antigen expression in the pathogenesis of the TGF-beta 1 null mouse phenotype," Proc Natl Acad Sci U S A. Nov. 1, 1993;90(21):9944-8.
Gérard C, et al. "Interleukin 10 reduces the release of tumor necrosis factor and prevents lethality in experimental endotoxemia," J Exp Med. Feb. 1, 1993;177(2):547-50.
Girol AP, et al. "Anti-inflammatory mechanisms of the annexin A1 protein and its mimetic peptide Ac2-2 6 in models of ocular inflammation in vivo and in vitro," J Immunol. Jun. 1, 2013;190(11):5689-701.
Go NF, et al. "Interleukin 10, a novel B cell stimulatory factor: unresponsiveness of X chromosome-linked immunodeficiency B cells," J Exp Med. Dec. 1, 1990;172(6):1625-31.
Gonzalez S, et al. "Genetic engineering of cytolytic T lymphocytes for adoptive T-cell therapy of neuroblastoma," J Gene Med. Jun. 2004;6(6):704-11.
Griffioen M, et al. "Retroviral transfer of human CD20 as a suicide gene for adoptive T-cell therapy," Haematologica. Sep. 2009;94(9):1316-20.
Hart PH, et al. "Potential antiinflammatory effects of interleukin 4: suppression of human monocyte tumor necrosis factor alpha, interleukin 1, and prostaglandin E2," Proc Natl Acad Sci USA. May 1989;86(10):3803-7.
Holland MJ, et al. "Proteins secreted by the parasitic nematode Nippostrongylus brasiliensis act as adjuvants for Th2 responses," Eur J Immunol. Jul. 2000;30(7):1977-87.
Hombach AA, et al. "OX40 costimulation by a chimeric antigen receptor abrogates CD28 and IL-2 induced IL-10 secretion by redirected CD4(+) T cells," Oncoimmunology. Jul. 1, 2012;1(4):458-466.
Horsfall AC, et al. "Suppression of collagen-induced arthritis by continuous administration of IL-4," J Immunol. Dec. 1, 1997;159(11):5687-96.
Hsu DH, et al. "Differential effects of IL-4 and IL-10 on IL-2-induced IFN-gamma synthesis and lymphokine-activated killer activity," Int Immunol. May 1992;4(5):563-9.
Hsu DH, et al. "Expression of interleukin-10 activity by Epstein-Barr virus protein BCRF1," Science. Nov. 9, 1990;250(4982):830-2.
Huang CH, et al. "Airway inflammation and IgE production induced by dust mite allergen-specific memory/effector Th2 cell line can be effectively attenuated by IL-35," J Immunol. Jul. 1, 2011;187(1):462-71.
Introna M, et al. "Genetic modification of human T cells with CD20: a strategy to purify and lyse transduced cells with anti-CD20 antibodies," Hum Gene Ther. Mar. 1, 2000;11(4):611-20.
Jenkins C, et al. "Immunomodulatory properties of a viral homolog of human interleukin-10 expressed by human cytomegalovirus during the latent phase of infection," J Virol. Apr. 2008;82(7):3736-50.
Jensen M, et al. "CD20 is a molecular target for scFvFc:zeta receptor redirected T cells: implications for cellular immunotherapy of CD20+ malignancy," Biol Blood Marrow Transplant. 1998;4(2):75-83.
John M, et al. "Expression and release of interleukin-8 by human airway smooth muscle cells: inhibition by Th-2 cytokines and corticosteroids," Am J Respir Cell Mol Biol. Jan. 1998;18(1):84-90.
John M, et al. "Human airway smooth muscle cells express and release RANTES in response to T helper 1 cytokines: regulation by T helper 2 cytokines and corticosteroids," J Immunol. Feb. 15, 1997;158(4):1841-7.
Joosten LA, et al. "Role of interleukin-4 and interleukin-10 in murine collagen-induced arthritis. Protective effect of interleukin-4 and interleukin-10 treatment on cartilage destruction," Arthritis Rheum. Feb. 1997;40(2):249-60.
Jovanovic D, et al. "Effect of IL-13 on cytokines, cytokine receptors and inhibitors on human osteoarthritis synovium and synovial fibroblasts," Osteoarthritis Cartilage. Jan. 1998;6(1):40-9.
Jungo F, et al. "IFN-beta inhibits the ability of T lymphocytes to induce TNF-alpha and IL-1beta production in monocytes upon direct cell-cell contact," Cytokine. Jun. 7, 2001;14(5):272-82.
Kahlon KS, et al. "Specific recognition and killing of glioblastoma multiforme by interleukin 13-zetakine redirected cytolytic T cells," Cancer Res. Dec. 15, 2004;64(24):9160-6.
Keravala A, et al. "Human, viral or mutant human IL-10 expressed after local adenovirus-mediated gene transfer are equally effective in ameliorating disease pathology in a rabbit knee model of antigen-induced arthritis," Arthritis Res Ther. 2006;8(4):R91.
Keystone E, et al. "IL-10 as a therapeutic strategy in the treatment of rheumatoid arthritis," Rheum Dis Clin North Am. Aug. 1998;24(3):629-39.
Kim KN, et al. "Viral IL-10 and soluble TNF receptor act synergistically to inhibit collagen-induced arthritis following adenovirus-mediated gene transfer," J Immunol. Feb. 1, 2000;164(3):1576-81.
Kochetkova I, et al. "IL-35 stimulation of CD39+ regulatory T cells confers protection against collagen II-induced arthritis via the production of IL-10," J Immunol. Jun. 15, 2010;184(12):7144-53.
Kuruvilla AP, et al. "Protective effect of transforming growth factor beta 1 on experimental autoimmune diseases in mice," Proc Natl Acad Sci U S A. Apr. 1, 1991;88(7):2918-21.
Lang P, et al. "Chimeric CD19 antibody mediates cytotoxic activity against leukemic blasts with effector cells from pediatric patients who received T-cell-depleted allografts," Blood. May 15, 2004;103(10):3982-5.
Li DK, et al. "Magnetic resonance imaging results of the PRISMS trial: a randomized, double-blind, placebo-controlled study of interferon-beta1a in relapsing-remitting multiple sclerosis. Prevention of Relapses and Disability by Interferon-beta1a Subcutaneously in Multiple Sclerosis," Ann Neurol. Aug. 1999;46(2):197-206.
Liu W, et al. "CD127 expression inversely correlates with FoxP3 and suppressive function of human CD4+ T reg cells," J Exp Med. Jul. 10, 2006;203(7):1701-11.
Liu Y, et al. "Expression cloning and characterization of a human IL-10 receptor," J Immunol. Feb. 15, 1994;152(4):1821-9.
Ma Y, et al. "Inhibition of collagen-induced arthritis in mice by viral IL-10 gene transfer," J Immunol. Aug. 1, 1998;161(3):1516-24.
MacNeil IA, et al. "IL-10, a novel growth cofactor for mature and immature T cells," J Immunol. Dec. 15, 1990;145(12):4167-73.
Maiti SN, et al. "Sleeping beauty system to redirect T-cell specificity for human applications," J Immunother. Feb. 2013;36(2):112-23.
Makhija R, et al. "Cytokine storm in acute pancreatitis," J Hepatobiliary Pancreat Surg. 2002;9(4):401-10.
Marfaing-Koka A, et al. "Regulation of the production of the RANTES chemokine by endothelial cells. Synergistic induction by IFN-gamma plus TNF-alpha and inhibition by IL-4 and IL-13," J Immunol. Feb. 15, 1995;154(4):1870-8.
Marodon G, et al. "Specific transgene expression in human and mouse CD4+ cells using lentiviral vectors with regulatory sequences from the CD4 gene," Blood. May 1, 2003;101(9):3416-23.

(56) References Cited

OTHER PUBLICATIONS

Martel-Pelletier J, et al. "Cytokines and their role in the pathophysiology of osteoarthritis," Front Biosci. Oct. 15, 1999;4:D694-703.
McNamee EN, et al. "Interleukin 37 expression protects mice from colitis," Proc Natl Acad Sci U S A. Oct. 4, 2011;108(40):16711-6.
Minter RM, et al. "Adenoviral delivery of human and viral IL-10 in murine sepsis," J Immunol. Jul. 15, 2001;167(2):1053-9.
Minty A, et al. "Interleukin-13 is a new human lymphokine regulating inflammatory and immune responses," Nature. Mar. 18, 1993;362(6417):248-50.
Mulligan MS, et al. "Protective effects of IL-4, IL-10, IL-12, and IL-13 in IgG immune complex-induced lung injury: role of endogenous IL-12," J Immunol. Oct. 1, 1997;159(7):3483-9.
Muniappan A, et al. "Ligand-mediated cytolysis of tumor cells: use of heregulin-zeta chimeras to redirect cytotoxic T lymphocytes," Cancer Gene Ther. Jan. 2000;7(1):128-34.
Nicoletti F, et al. "Prevention of endotoxin-induced lethality in neonatal mice by interleukin-13," Eur J Immunol. Jun. 1997;27(6):1580-3.
Niedbala W, et al. "IL-35 is a novel cytokine with therapeutic effects against collagen-induced arthritis through the expansion of regulatory T cells and suppression of Th17 cells," Eur J Immunol. Nov. 2007;37(11):3021-9.
Nold MF, et al. "IL-37 is a fundamental inhibitor of innate immunity," Nat Immunol. Nov. 2010;11(11):1014-22.
Oberholzer C, et al. "Targeted adenovirus-induced expression of IL-10 decreases thymic apoptosis and improves survival in murine sepsis," Proc Natl Acad Sci U S A. Sep. 25, 2001;98(20):11503-8.
Ossege LM, et al. "Immunomodulatory effects of interferon-beta-1b in patients with multiple sclerosis," Int Immunopharmacol. Jun. 2001;1(6):1085-100.
Palmer G, et al. "Interferon beta stimulates interleukin 1 receptor antagonist production in human articular chondrocytes and synovial fibroblasts," Ann Rheum Dis. Jan. 2004;63(1):43-9.
Pameijer CR, et al. "Conversion of a tumor-binding peptide identified by phage display to a functional chimeric T cell antigen receptor," Cancer Gene Ther. Jan. 2007;14(1):91-7.
Parente-Pereira AC, et al. "Trafficking of CAR-engineered human T cells following regional or systemic adoptive transfer in SCID beige mice," J Clin Immunol. Aug. 2011;31(4):710-8.
Patel SD, et al. "Impact of chimeric immune receptor extracellular protein domains on T cell function," Gene Ther. Mar. 1999;6(3):412-9.
Pennline KJ, et al. "Recombinant human IL-10 prevents the onset of diabetes in the nonobese diabetic mouse," Clin Immunol Immunopathol. May 1994;71(2):169-75.
Perdomo OJ, et al. "Acute inflammation causes epithelial invasion and mucosal destruction in experimental shigellosis," J Exp Med. Oct. 1, 1994;180(4):1307-19.
Perretti M, et al. "Annexin A1 and glucocorticoids as effectors of the resolution of inflammation," Nat Rev Immunol. Jan. 2009;9(1):62-70.
Persson S, et al. "Interleukin-10 suppresses the development of collagen type II-induced arthritis and ameliorates sustained arthritis in rats," Scand J Immunol. Dec. 1996;44(6):607-14.
Pflanz S, et al. "IL-27, a heterodimeric cytokine composed of EBI3 and p28 protein, induces proliferation of naive CD4+ T cells," Immunity. Jun. 2002;16(6):779-90.
Pritchard DI, et al. "Immunosuppressive proteins secreted by the gastrointestinal nematode parasite *Heligmosomoides polygyrus*," Int J Parasitol. Jul. 1994;24(4):495-500.
Punnonen J, et al. "IL-13 induces proliferation, Ig isotype switching, and Ig synthesis by immature human fetal B cells," J Immunol. Feb. 1, 1994;152(3):1094-102.
Rep MH, et al. "Interferon (IFN)-beta treatment enhances CD95 and interleukin 10 expression but reduces interferon-gamma producing T cells in MS patients," J Neuroimmunol. Apr. 1, 1999;96(1):92-100.
Rep MH, et al. "Recombinant interferon-beta blocks proliferation but enhances interleukin-10 secretion by activated human T-cells," J Neuroimmunol. Jul. 1996;67(2):111-8.
Reth M. "Pillars article: antigen receptor tail clue. Nature. 1989. 338: 383-384," J Immunol. May 1, 2014;192(9):4015-6.
Rott O, et al. "Interleukin-10 prevents experimental allergic encephalomyelitis in rats," Eur J Immunol. Jun. 1994;24(6):1434-40.
Ruuls SR, et al. "Cytokine-directed therapies in multiple sclerosis and experimental autoimmune encephalomyelitis," Immunol Cell Biol. Feb. 1998;76(1):65-73.
Schambach A, et al. "Design and production of retro- and lentiviral vectors for gene expression in hematopoietic cells," Methods Mol Biol. 2009;506:191-205.
Sharma S, et al. "The IL-1 family member 7b translocates to the nucleus and down-regulates proinflammatory cytokines," J Immunol. Apr. 15, 2008;180(8):5477-82.
Singh H, et al. "Redirecting specificity of T-cell populations for CD19 using the Sleeping Beauty system," Cancer Res. Apr. 15, 2008;68(8):2961-71.
Sinn PL, et al. "Gene therapy progress and prospects: development of improved lentiviral and retroviral vectors—design, biosafety, and production," Gene Ther. Jul. 2005;12(14):1089-98.
Skerra A, et al. "Assembly of a functional immunoglobulin Fv fragment in *Escherichia coli*," Science. May 20, 1988;240(4855):1038-41.
Slobedman B, et al. "Virus-encoded homologs of cellular interleukin-10 and their control of host immune function," J Virol. Oct. 2009;83(19):9618-29.
Smith VP, et al. "Ectromelia, vaccinia and cowpox viruses encode secreted interleukin-18-binding proteins," J Gen Virol. May 2000;81(Pt 5):1223-30.
Song DG, et al. "In vivo persistence, tumor localization, and antitumor activity of CAR-engineered T cells is enhanced by costimulatory signaling through CD137 (4-1BB)," Cancer Res. Jul. 1, 2011;71(13):4617-27.
Stumhofer JS, et al. "Interleukin 27 negatively regulates the development of interleukin 17-producing T helper cells during chronic inflammation of the central nervous system," Nat Immunol. Sep. 2006;7(9):937-45.
Stumhofer JS, et al. "Interleukins 27 and 6 induce STAT3-mediated T cell production of interleukin 10," Nat Immunol. Dec. 2007;8(12):1363-71.
Tak PP, et al. "The effects of interferon beta treatment on arthritis," Rheumatology (Oxford). Apr. 1999;38(4):362-9.
Tanaka Y, et al. "Effect of IL-10 on collagen-induced arthritis in mice," Inflamm Res. Jun. 1996;45(6):283-8.
Terakura S, et al. "Generation of CD19-chimeric antigen receptor modified CD8+ T cells derived from virus-specific central memory T cells," Blood. Jan. 5, 2012;119(1):72-82.
Tey SK, et al. "Inducible caspase 9 suicide gene to improve the safety of allodepleted T cells after haploidentical stem cell transplantation," Biol Blood Marrow Transplant. Aug. 2007;13(8):913-24.
Thomis DC, et al. "A Fas-based suicide switch in human T cells for the treatment of graft-versus-host disease," Blood. Mar. 1, 2001;97(5):1249-57.
Topalian SL, et al. "Therapy of cancer using the adoptive transfer of activated killer cells and interleukin-2," Acta Haematol. 1987;78 Suppl 1:75-6.
Turner M, et al. "Induction of the interleukin 1 receptor antagonist protein by transforming growth factor-beta," Eur J Immunol. Jul. 1991;21(7):1635-9.
Urbanska K, et al. "A universal strategy for adoptive immunotherapy of cancer through use of a novel T-cell antigen receptor," Cancer Res. Apr. 1, 2012;72(7):1844-52.
Van Deventer SJ, et al. "Multiple doses of intravenous interleukin 10 in steroid-refractory Crohn's disease. Crohn's Disease Study Group," Gastroenterology. Aug. 1997;113(2):383-9.
Van Holten J, et al. "Treatment with recombinant interferon-beta reduces inflammation and slows cartilage destruction in the collagen-induced arthritis model of rheumatoid arthritis," Arthritis Res Ther. 2004;6(3):R239-49.

(56) References Cited

OTHER PUBLICATIONS

Van Laethem JL, et al. "Interleukin 10 prevents necrosis in murine experimental acute pancreatitis," Gastroenterology 1995; 108:1917-22.
Van Lent PL, et al. "Local overexpression of adeno-viral IL-4 protects cartilage from metallo proteinase-induced destruction during immune complex-mediated arthritis by preventing activation of pro-MMPs," Osteoarthritis Cartilage. Mar. 2002;10(3):234-43.
Van Meegeren ME, et al. "IL-4 alone and in combination with IL-10 protects against blood-induced cartilage damage," Osteoarthritis Cartilage. Jul. 2012;20(7):764-72.
Vieira P, et al. "Isolation and expression of human cytokine synthesis inhibitory factor cDNA clones: homology to Epstein-Barr virus open reading frame BCRFI," Proc Natl Acad Sci U S A. Feb. 15, 1991;88(4):1172-6.
Vodovotz Y, et al. "Spontaneously increased production of nitric oxide and aberrant expression of the inducible nitric oxide synthase in vivo in the transforming growth factor beta 1 null mouse," J Exp Med. May 1, 1996;183(5):2337-42.
Ward, E. S., et al. "Binding activities of a repertoire of single immunoglobulin variable domains secreted from *Escherichia coli*," (1989) Nature, 341(6242), 544-546.
Wirtz S, et al. "Interleukin-35 mediates mucosal immune responses that protect against T-cell-dependent colitis," Gastroenterology. Nov. 2011;141(5):1875-86.
Yang Z, et al. "Suppression of autoimmune diabetes by viral IL-10 gene transfer," J Immunol. Jun. 15, 2002;168(12):6479-85.
Yong VW, et al. "Interferon beta in the treatment of multiple sclerosis: mechanisms of action," Neurology. Sep. 1998;51(3):682-9.
Zandian M, et al. "Use of cytokine immunotherapy to block CNS demyelination induced by a recombinant HSV-1 expressing IL-2," Gene Ther. Jul. 2011;18(7):734-42.
Zhang L, et al. "Improving adoptive T cell therapy by targeting and controlling IL-12 expression to the tumor environment," Mol Ther. Apr. 2011;19(4):751-9.
Zhang T, et al. "An NKp30-based chimeric antigen receptor promotes T cell effector functions and antitumor efficacy in vivo," J Immunol. Sep. 1, 2012;189(5):2290-9.
Zhang T, et al. "Mouse tumor vasculature expresses NKG2D ligands and can be targeted by chimeric NKG2D-modified T cells," J Immunol. Mar. 1, 2013;190(5):2455-63.
Zhao Y, et al. "High-efficiency transfection of primary human and mouse T lymphocytes using RNA electroporation," Mol Ther. Jan. 2006;13(1):151-9.
Zhao Y, et al. "Multiple injections of electroporated autologous T cells expressing a chimeric antigen receptor mediate regression of human disseminated tumor," Cancer Res. Nov. 15, 2010;70(22):9053-61.
Geiger TL, et al. "Integrated src kinase and costimulatory activity enhances signal transduction through single-chain chimeric receptors in T lymphocytes," Integrated src kinase and costimulatory activity enhances signal transduction through single-chain chimeric receptors in T lymphocytes, Blood, Oct. 15, 2001 z vol. 98, No. 8, pp. 2364-2371.
Scholler J, et al. "Decade-long safety and function of retroviral-modified chimeric antigen receptor T cells," Decade-long safety and function of retroviral-modified chimeric antigen receptor T cells, Sci Transl Med. May 2, 2012; 4(132): pp. 1-16.
Song DG, et al. "CD27 costimulation augments the survival and antitumor activity of redirected human T cells in vivo," CD27 costimulation augments the survival and antitumor activity of redirected human T cells in vivo, Blood, Jan. 19, 2012 • vol. 119, No. 3, pp. 696-708.
Spencer JV, et al. "Stimulation of B lymphocytes by cmvIL-10 but not LAcmvIL-10," Stimulation of B lymphocytes by cmvIL-10 but not LAcmvIL-10, Virology. Apr. 25, 2008; 374(1): 164-169.
Yanagawa H, et al. "Contrasting effect of interleukin-13 on interleukin-1 receptor antagonist and proinflammatory cytokine production by human alveolar macrophages," Contrasting effect of interleukin-13 on interleukin-1 receptor antagonist and proinflammatory cytokine production by human alveolar macrophages, Am. J. Respir. Cell Nol. Biol. vol. 12. pp. 71-76, 1995.
"T lymphocyte surface glycoprotein (CD8-beta) precursor" (GENBANK Accession No. AAA35664), 1993. 2 pages.
"Equine herpesvirus 2 IL-10" (GENBANK Accession No. AAB26148), 1993. 1 page.
"Orf virus IL-10" (GENBANK Accession No. AAC57332), 1997. 1 page.
"Baboon lymphocryptovirus IL-10" (GENBANK Accession No. AAF23949), 2016. 1 page.
"Human herpes 5 IL-10/UL111A" GENBANK Accession No. AAF36285, 2000. 1 page.
"African green monkey cytomegalovirus vIL-10" (GENBANK Accession No. AAF63435), 2000. 1 page.
"Baboon cytomegalovirus IL-10-like protein" (GENBANK Accession No. AAF63436), 2000. 1 page.
"Rhesus lymphocryptovirus BCFRI" (GENBANK Accession No. AAK95412), 2002. 2 pages.
"Lumpy skin disease virus IL-10" (GENBANK Accession No. AAN02729), 2003. 1 page.
"Human herpes 5 IL-10/UL111A" GENBANK Accession No. AAR31656, 2013. 3 pages.
"Ovine herpesvirus 2 IL-10" (GENBANK Accession No. ABB22222), 2006. 1 page.
"Human herpesvirus 5 latency associated cmvIL-10" (GENBANK Accession No. ACR49217), 2009. 1 page.
"Nippostrongylus brasiliensis C-type lectin-2" (GENBANK Accession No. ACS377230, 2009. 1 page.
"Rhesus cytomegalovirus ULIIIA/vIL-10" (GENBANK Accession No. AF200417), 2000. 2 page.
"Epstein-Barr virus protein BCRFI" (GENBANK Accession No. CAD53385), 2016. 4 pages.
"Heligmosomoides polygyrus C-type lectin-1" (GENBANK Accession No. FJ456978), 2009. 1 page.
"T-cell surface glycoprotein CD3y chain precursor" (GENBANK Accession No. NP_000064, 2019. 5 pages.
"High affinity immunoglobulin epsilon (FceRI β) receptor subunit beta isoform," GENBANK Accession No. NP_0001300, 2019. 5 pages.
"Human IL-10" GENBANK Accession No. NP_000563, 2020. 4 pages.
"Human 1L-Ira" GENBANK Accession No. NP__000568, 2020. 4 pages.
"Human IL-4" GENBANK Accession No. NP__000580, 2019. 4 pages.
CD79b (GENBANK Accession No. NP_000611), 2019. 6 pages.
"Human TGF-β1" GENBANK Accession No. NP_000651, 2020. 5 pages.
"CD35" (GENBANK Accession No. NP_000723), 2019. 5 pages.
"CD3e" (GENBANK Accession No. NP 000724), 2019. 4 pages.
"Human IL-12a" GENBANK Accession No. NP_000873, 2019. 4 pages.
"CD137" (4-1BB, GENBANK Accession No. NP_001552), 2019. 5 pages.
"CD2" (GENBANK Accession No. NP___001758), 2019. 5 pages.
"CD8a" (GENBANK Accession No. NP_001759.3), 2020. 4 pages.
"CD22" (GENBANK Accession No. NP_001762), 2019. 7 pages.
"CD79a" (GENBANK Accession No. NP_001774), 2019. 5 pages.
"CD66d" (GENBANK Accession No. NP_001806), 2019. 4 pages.
"Human IFN-β" GENBANK Accession No. NP_002167, 2019. 4 pages.
"Human IL-13" GENBANK Accession Nos. NP_002179, 2019. 3 pages.
"CD134" (OX40, GENBANK Accession No. NP__003318), 2020. 5 pages.
"FceRIy" (GENBANK Accession No. NP_004097), 2019. 4 pages.
"GITR" (GENBANK Accession No. NP_004186), 2019. 5 pages.
"EBI3" GENBANK Accession No. NP_005755, 2019. 4 pages.
"ICOS" (GENBANK Accession No. NP_036224), 2020. 4 pages.
"CD5" (GENBANK Accession No. NP_055022), 2019. 5 pages.
"Human IL-37b" GENBANK Accession No. NP__055254; 2019. 4 pages.

(56) References Cited

OTHER PUBLICATIONS

"Sheeppox virus IL-10" (GENBANK Accession No. NP_659579), 2018. 2 pages.
"Human IL-27" GENBANK Accession No. NP_663634, 2019. 4 pages.
"Human IL-4" GENBANK Accession No. NP_758858, 2020. 4 pages.
"Human IL-37d" GENBANK Accession No. NP_775294, 2019. 4 pages.
"Interleukin-37 isoform 3" GENBANK Accession No. NP 775295, 2019. 4 pages.
"Human IL-37c" GENBANK Accession No. NP_775296; 2019. 4 pages.
"Human IL-Ira" GENBANK Accession No. NP_776213, 2020. 4 pages.
"Interleukin-1 receptor antagonist protein isoform 1 precursor" GENBANK Accession No. NP_776214, 2020. 4 pages.
"T-cell surface glycoprotein CD3 zeta chain isoform 1 precursor," (GENBANK Accession No. NP_932170), 2020. 5 pages.
"Epstein-Barr virus protein BCRFI" (GENBANK Accession No. P03180), 2019. 4 pages.
"Pan paniscus viral IL-10 homolog" (GENBANK Accession No. XP_003804206), 2012. 1 page.
"Human herpes 5 IL-10/UL111A" GENBANK Accession No. YP_081552, 2018. 3 pages.
"Koi herpesvirus IL-10" (GENBANK Accession No. YP_001096169), 2018. 2 pages.
"Goatpoxvirus IL-10" (GENBANK Accession No. YP_001293197 ), 2018. 2 pages.
"Interleukin-37 isoform 5 [*Homo sapiens*]" GENBANK Accession No. NP_775297; 2 019. 3 pages.

\* cited by examiner

SEQUENCE LISTING

<160> NUMBER OF SEQ ID NOS: 13

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide

<400> SEQUENCE: 1

Gly Gly Gly Ser Gly Gly Gly Ser Gly Gly Gly Ser Gly Gly Gly Ser
1               5                   10                  15

```
<210> SEQ ID NO 2
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes Asp or Glu.
<220> FEATURE:
<221> NAME/KEY: MISC_FEATURE
<222> LOCATION: (2)..(3)
<223> OTHER INFORMATION: Xaa denotes any amino acid residue.
<220> FEATURE:
<221> NAME/KEY: MISC_FEATURE
<222> LOCATION: (5)..(6)
<223> OTHER INFORMATION: Xaa denotes any amino acid residue.
<220> FEATURE:
<221> NAME/KEY: MISC_FEATURE
<222> LOCATION: (7)..(7)
<223> OTHER INFORMATION: Xaa denotes Ile or Leu.
<220> FEATURE:
<221> NAME/KEY: MISC_FEATURE
<222> LOCATION: (8)..(13)
<223> OTHER INFORMATION: Xaa denotes any amino acid residue.
<220> FEATURE:
<221> NAME/KEY: MISC_FEATURE
<222> LOCATION: (14)..(15)
<223> OTHER INFORMATION: Xaa can be present or absent and when present
     denotes any amino acid residue.
<220> FEATURE:
<221> NAME/KEY: MISC_FEATURE
<222> LOCATION: (17)..(18)
<223> OTHER INFORMATION: Xaa denotes any amino acid residue.
<220> FEATURE:
<221> NAME/KEY: MISC_FEATURE
<222> LOCATION: (19)..(19)
<223> OTHER INFORMATION: Xaa denotes Ile or Leu.

<400> SEQUENCE: 2

Xaa Xaa Xaa Tyr Xaa Xaa Xaa Xaa Xaa Xaa Xaa Xaa Xaa Xaa Xaa Tyr
1               5                   10                  15

Xaa Xaa Xaa

<210> SEQ ID NO 3
<211> LENGTH: 63
<212> TYPE: PRT
<213> ORGANISM: Artificial Sequence
<220> FEATURE:
<223> OTHER INFORMATION: Synthetic peptide

<400> SEQUENCE: 3

Gly Ser Gly Ser Arg Val Thr Glu Leu Leu Tyr Arg Met Lys Arg Ala
1               5                   10                  15

Glu Thr Tyr Cys Pro Arg Pro Leu Leu Ala Ile His Pro Thr Glu Ala
            20                  25                  30

Arg His Lys Gln Lys Ile Val Ala Pro Val Lys Gln Leu Leu Asn Phe
        35                  40                  45

Asp Leu Leu Lys Leu Ala Gly Asp Val Glu Ser Asn Pro Gly Pro
    50                  55                  60

<210> SEQ ID NO 4
<211> LENGTH: 25
<212> TYPE: PRT
<213> ORGANISM: Artificial Sequence
<220> FEATURE:
<223> OTHER INFORMATION: Synthetic peptide

<400> SEQUENCE: 4
```

Asp Gly Phe Cys Ile Leu Tyr Leu Leu Ile Leu Leu Met Arg Ser
1               5                   10                  15

Gly Asp Val Glu Thr Asn Pro Gly Pro
            20                  25

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

Leu Leu Cys Phe Met Leu Leu Leu Leu Ser Gly Asp Val Glu Leu
1               5                   10                  15

Asn Pro Gly Pro
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

His His Phe Met Phe Leu Leu Leu Leu Ala Gly Asp Ile Glu Leu
1               5                   10                  15

Asn Pro Gly Pro
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide

<400> SEQUENCE: 7

Trp Phe Leu Val Leu Leu Ser Phe Ile Leu Ser Gly Asp Ile Glu Val
1               5                   10                  15

Asn Pro Gly Pro
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide

<400> SEQUENCE: 8

Lys Asn Cys Ala Met Tyr Met Leu Leu Leu Ser Gly Asp Val Glu Thr
1               5                   10                  15

Asn Pro Gly Pro
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide

<400> SEQUENCE: 9

```
Met Val Ile Ser Gln Leu Met Leu Lys Leu Ala Gly Asp Val Glu Glu
1               5                   10                  15

Asn Pro Gly Pro
            20

<210> SEQ ID NO 10
<211> LENGTH: 22
<212> TYPE: PRT
<213> ORGANISM: Artificial Sequence
<220> FEATURE:
<223> OTHER INFORMATION: Synthetic peptide

<400> SEQUENCE: 10

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 11
<211> LENGTH: 21
<212> TYPE: PRT
<213> ORGANISM: Artificial Sequence
<220> FEATURE:
<223> OTHER INFORMATION: Synthetic peptide

<400> SEQUENCE: 11

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 12
<211> LENGTH: 23
<212> TYPE: PRT
<213> ORGANISM: Artificial Sequence
<220> FEATURE:
<223> OTHER INFORMATION: Synthetic peptide

<400> SEQUENCE: 12

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa denotes any amino acid residue.
<220> FEATURE:
<221> NAME/KEY: MISC_FEATURE
<222> LOCATION: (4)..(4)
<223> OTHER INFORMATION: Xaa denotes any amino acid residue.

<400> SEQUENCE: 13

Asp Xaa Glu Xaa Asn Pro Gly Pro
1               5
```

CHIMERIC ANTIGEN RECEPTOR ANTI-INFLAMMATORY CELLS AND METHODS OF USE

INTRODUCTION

This application is a U.S. National Stage Application of PCT/US2016/053893 filed Sep. 27, 2016 and claims the benefit of priority of U.S. Provisional Application No. 62/233,517, the contents of each of which are incorporated herein by reference in their entirety.

BACKGROUND

Although genetic modifications to stimulate the immune system are beneficial for battling infectious organisms and cancer, there also exists a set of devastating diseases that are caused by an over-zealous and unchecked immune response. The targeting of self-antigens under normal physiologic conditions can cause a range of serious ailments including type 1 diabetes, multiple sclerosis, rheumatoid arthritis, systemic lupus erythematosus, and autoimmune encephalomyelitis. A relatively new set of autoimmune diseases, categorized as autoinflammatory diseases, have also been characterized including familial Mediterranean fever (FMF), neonatal onset multisystem inflammatory disease (NOMID), tumor necrosis factor (TNF) receptor-associated periodic syndrome (TRAPS), deficiency of the Interleukin-1 receptor antagonist (DIRA) and Behcet's disease. Additional inflammatory diseases that cause morbidity and mortality in a large number of patients include inflammatory bowel disease (Crohn's disease and ulcerative colitis), chronic granulomatous disease (CGD), and the various forms of vasculitis.

In general, dampening the immune response is the ideal treatment for autoimmune and inflammatory diseases and current therapies revolve around the use of steroids, cytokine antagonists, or directly down-regulating the immune system using various modalities. Gene therapies may provide a viable biological alternative to directly blunt an overactive immune response. Over-expressing anti-inflammatory cytokines such as IL-10, TGF-$\beta$, IL-30, IL-35 or IL-37 in T cells or monocyte/dendritic cell populations ex vivo with a reinfusion of the modified cells has been suggested to aid in decreasing inflammatory driven symptoms (Kerkar (2013) *Frontiers Immunol.* 4:1-7; Mathisen et al. (1997) *J. Exp. Med.* 186:159-164). Another suggested alternative is to construct a decoy cytokine receptor that contains the correct receptor sequence to enable for binding of pro-inflammatory cytokines such as IL-12 combined with a non-functioning cytoplasmic signal transducing sequence. Over-expressing these "dominant-negative" receptors would enable reinfused immune cells to function as sinks for the inflammatory cytokines responsible for the pathophysiology of the disease.

US 2015/0038684 discloses a bispecific antigen receptor containing at least two antigen-specific targeting regions that target antigens specific for cancer, inflammatory disease, neuronal disorder, diabetes, cardiovascular disease, infectious disease, autoimmune disease, and combinations thereof.

Similarly, US 2010/0135974 describes a redirected regulatory T lymphocyte endowed with specificity toward a selected target antigen or ligand by expressing a chimeric receptor polypeptide. This reference indicates that the redirected regulatory T cells at sites of inflammation results in suppression of inflammatory conditions, commonly part of organ-specific autoimmune disease. In addition, this reference suggests that redirected regulatory T cells of the invention can be triggered or activated to release suppressive cytokines that will result in suppression of any "bystander" effector T-cells, and by this mechanism, quell an ongoing inflammatory/autoimmune response.

SUMMARY OF THE INVENTION

The invention provides an immune cell and nucleic acid constructs harboring nucleic acids encoding a chimeric antigen receptor and nucleic acids encoding at least one exogenous anti-inflammatory or immunosuppressant protein. In some embodiments, the cell is a T lymphocyte. In one embodiment, the chimeric antigen receptor is a single chain variable fragment. In another embodiment, the chimeric antigen receptor includes an antigen targeting domain or recognition domain that binds an antigen or ligand at a site of inflammation or autoimmunity and an immune signaling receptor containing an immunoreceptor tyrosine-based activation motif. In a further embodiment, the chimeric antigen receptor further includes a costimulatory endodomain. An anti-inflammatory or immunosuppressant protein includes a cytokine, a virokine (e.g., viral IL-10 protein) or a C-type lectin protein (e.g., a helminth C-type lectin protein). Further, in some embodiments, expression of the anti-inflammatory or immunosuppressant protein is regulated by a promoter that is enhanced by signaling from the chimeric antigen receptor. A method for treating inflammation or immune-mediated autoimmunity using an immune cell of the invention and kits containing one or more immune cells or the nucleic acid construct of the invention are also provided.

DETAILED DESCRIPTION OF THE INVENTION

Figure 1:
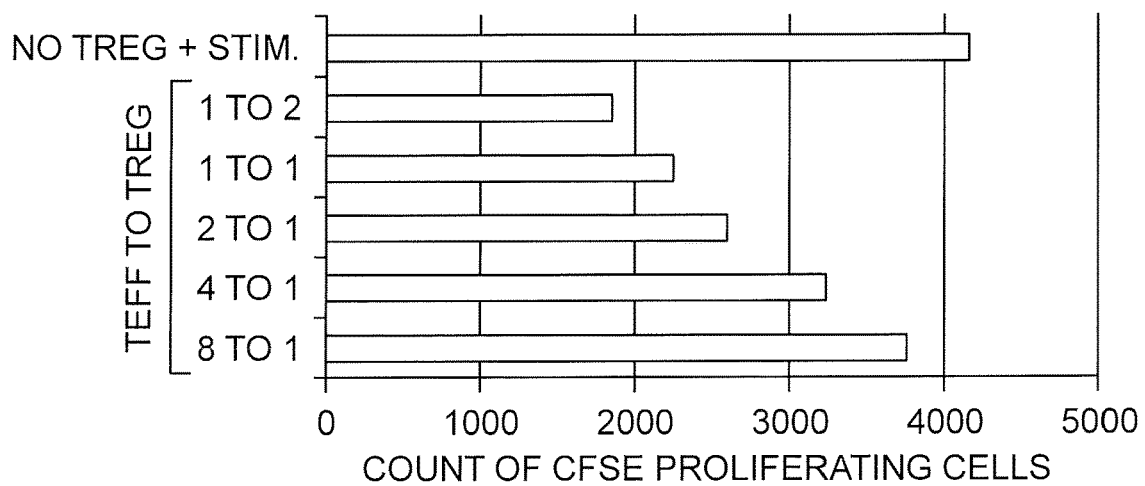
FIG. 1 shows that CD4+ CD25+ CD127− Foxp3+ Treg cells (Treg) incubated in the presence of stimulus (Stim) and carboxyfluorescein succinimidyl ester (CFSE)-labeled CD4+ T cells (Teff) are capable of suppressing CD4+ T cell proliferation in a dose dependent manner, as measured by CFSE dilution assays.

The present invention is directed to chimeric immune cells that reduce or inhibit inflammation and subsequent tissue damage. In particular, this invention provides chimeric immune cells that secrete at least one anti-inflammatory or immunosuppressant protein that inhibits or reduces a proliferative and/or proinflammatory immune response preferentially at the site of inflammation or immune-mediated autoimmunity. In addition to an anti-inflammatory or immunosuppressant protein, the immune cells express a chimeric antigen receptor (CAR) that binds a specific ligand(s) expressed at the site of inflammation and/or autoimmunity. Binding of the CAR to the ligand(s) allows the chimeric immune cells to localize and become activated at the site of tissue damage. Secretion of the anti-inflammatory or immunosuppressant protein by the activated CAR cells suppresses the activation and function of local immune cells thereby reducing or inhibiting an immune response. The chimeric immune regulatory cells of this invention are useful in the treatment or amelioration of diseases where chronic inflammation or immune-mediated autoimmunity leads to tissue destruction and/or disease progression.

This invention provides nucleic acid constructs and immune cells, which harbor nucleic acids encoding a CAR and nucleic acids encoding an anti-inflammatory or immunosuppressant protein. As used herein, "anti-inflammatory," and "immunosuppressant" or "immunosuppressive" protein refers to a protein that inhibits local immune responses. Such immune responses include vasodilatation; leukocyte infiltration; redness; heat; activation of local cells and immune cells; expression of major histocompatibility complex (MHC) class II molecules, costimulatory molecules (e.g., B7-1 and B7-2), and adhesion proteins (e.g., ICAM-1); IL-1 induced proliferation; and the release of pro-inflammatory cytokines (e.g., IL-1, IL-2, IL-6, IL-8, IL-12, GM-CSF and TNF-α) and/or inflammatory mediators (e.g., NO, free radicals, prostaglandins and metalloproteases) from these cells. Further, "anti-inflammatory" and "immunosuppressant" or "immunosuppressive" protein refers to a protein that affects the diseased area by suppressing or countering immunologic and/or pro-inflammatory activities. In certain embodiments, the anti-inflammatory or immunosuppressant protein is selected for having minimal or no immune activation or immunostimulatory activity. By way of illustration, whereas human IL-10 can costimulate thymocyte and mast cell proliferation and B cell MHC class II expression, viral IL-10 cannot (Vieira, et al. (1991) *Proc. Natl. Acad. Sci. USA.* 88:1172-1176; MacNeil, et al. (1990) *J. Immunol.* 145:4167-4173; Fei, et al. (1990) *J. Exp. Med.* 172:1625-1631). Accordingly, while some embodiments embrace a human anti-inflammatory or immunosuppressant protein, in other embodiments, the anti-inflammatory or immunosuppressant protein is a non-human or non-mammalian protein.

The anti-inflammatory or immunosuppressant protein is exogenous in the sense that the recipient host cell (i.e., immune cell) either does not naturally express the anti-inflammatory or immunosuppressant protein or does not express the anti-inflammatory or immunosuppressant protein in concert with a CAR, e.g., on the same chimeric nucleic acid construct, from the same promoter, and/or from a promoter that is dependent upon CAR signaling.

Anti-inflammatory or immunosuppressant proteins of use in this invention include cytokines, virokines and C-type lectin proteins. Examples of anti-inflammatory or immunosuppressant cytokines include, but are not limited to, human Interleukin (IL)-10, IL-4, IL-35, IL-37, IL-27, IL-13, IL-1 receptor antagonist (IL-1ra), Interferon β (IFN-β), and Transforming Growth Factor β (TGF-β). An exemplary virokine is viral IL-10. Examples of anti-inflammatory or immunosuppressant C-type lectin proteins include helminth C-type lectin proteins such as *Heligmosomoides polygyrus* C-type lectin-1 (Hp-CTL-1) and *Nippostrongylus brasiliensis* C-type lectin-2 (Nb-CTL-2).

Human IL-10, also referred to as cellular IL-10 (cIL-10), exerts its function both directly and indirectly through upregulation of molecules including IL-1 receptor antagonists (IL-1ra) and soluble tumor necrosis factor α (TNF-α) receptor (sTNFR) and down-regulation of IL-8 and MCP-1 levels (Makhija & Kingsnorth (2002) *J. Hepatobiliary. Pancreat. Surg.* 4:401-410; Bhatia, et al. (2005) *Pancreatology* 2-3:132-144). Ultimately, the net effect is downregulation of macrophages, neutrophils, and CD4+ T cells, decreased antigen presentation, augmented CD8+ T cell cytolytic activity, and enhanced proliferation/differentiation of B cells. IL-10 has been shown to provide beneficial effects in TH1-mediated models diseases including experimental allergic encephalomyelitis ((EAE) Dai, et al. (2012) *J. Neuroimmunol.* 245(1-2):1-7; Rott, et al. (1994) *Eur. J. Immunol.* 24:1434-1440); pancreatitis (Van Laethem, et al. (1995) *Gastroenterology* 108:1917-1922), diabetes mellitus (Pennline, et al. (1994) *Clin. Immunol. Immunopathol.* 71:169-175), and experimental endotoxemia (Gerard, et al. (1993) *J. Exp. Med.* 177:547-550). IL-10 has also been effective in various animal models of arthritis, in reducing inflammation, in cellular infiltrates, and in joint destruction (Persson, et al. (1996) *Scand. J. Immunol.* 44:607-614; Tanaka, et al. (1996) *Inflamm. Res.* 45:283-288). These models have provided the basis for human trials in diseases such as multiple sclerosis, rheumatoid arthritis, psoriasis and Crohn's disease (Van Deventer, et al. (1997) *Gastroenterology* 113:383-389; Keystone, et al. (1998) *Rheum. Dis. Clin. N. Am.* 24:629-39; Asadullah, et al. (1998) *J. Clin. Investig.* 101:783-794). Exemplary IL-10 proteins of use in this invention include, but are not limited to, human IL-10 (GENBANK Accession No. NP 000563).

Like IL-10, human IL-4 is an important member of the TH2 family of anti-inflammatory cytokines, which has been shown to inhibit the ability of human monocytes to product TNF-α, IL-1 and prostaglandin $E_2$ (Hart, et al. (1989) *Proc. Natl. Acad. Sci. USA* 86:3803-3807; Essner, et al. (1989) *J. Immunol.* 142(11):3857-61). Because IL-4 antagonizes the effects of IL-12, a macrophage-derived cytokine promoting TH1 development, IL-4 represents an important regulator of the TH1/TH2 balance. The activity of IL-4 has been studied in several animal models of TH1-mediated autoimmunity, including CIA and streptococcal cell wall-induced arthritis (Horsfall, et al. (1997) *J. Immunol.* 159(11):5687-96; Allen, et al. (1993) *J. Immunol.* 151:4344-4351). Further, local expression of IL-4 has been shown to protect against metalloproteinase-induced cartilage destruction during immune complex-mediated arthritis (van Lent, et al. (2002) *Osteoarthritis Cartilage* 10(3):234-43). In addition, IL-4 has been shown to synergize with IL-10 to limit mononuclear cell infiltration of synovial tissue and prevent cartilage degradation (van Meegeren, et al. (2012) *Osteoarthritis Cartilage* 20(7):764-772; Joosten, et al. (1997) *Arthritis Rheum.* 40:249-260). Therefore, the combined use of IL-4 and IL-10 is expected to be of particular use in the treatment of human autoimmune disease. Exemplary IL-4 proteins of use in this invention include, e.g., human IL-4 available under GENBANK Accession Nos. NP_000580 and NP_758858.

Human IL-35 is a heterodimeric protein with two subunits, IL-12α (also known as IL-12p35) and Epstein-Barr virus induced 3 (EBI3; also known as IL-27β) (Collison & Vignali (2008) *Immunol. Rev.* 226:248-262; Collison, et al. (2007) *Nature* 450:566-569; Devergne, et al. (1997) *Proc. Natl. Acad. Sci. USA* 94:12041-6). IL-35 down-regulates Th17 cell development and inhibits autoimmune inflammation and has been shown to inhibit inflammation in various autoimmunity models such as experimental colitis (Collison, et al. (2007) *Nature* 450:566-569; Wirtz, et al. (2011) *Gastroenerology* 141:1875-86), collagen-induced autoimmune arthritis (Niedbala, et al. (2007) *Eur. J. Immunol.* 37:3021-3029; Kochetkova, et al. (2010) *J. Immunol.* 184: 7144-53), autoimmune demyelination in central nervous system (Zandian, et al. (2011) *Gene Ther.* 18:734-42), and type 2 T helper cell (Th2)-mediated allergic asthma (Huang, et al. (2011) *J. Immunol.* 187:462-71). An exemplary IL-35 protein of use in this invention can be prepared using, e.g., human IL-12α available under GENBANK Accession No. NP_000873, and EBI3 available under GENBANK Accession No. NP_005755. The IL-12α and EBI3 proteins of IL-35 can be expressed as separate proteins or as a single chain protein (Collison, et al. (2007) *Nature* 450:566-9). When expressed as a single chain protein, the IL-12α and EBI3 proteins can be directly fused to one another as a contiguous protein sequence or fused together via a linker, e.g., (GGGS)$_4$ (SEQ ID NO:1).

IL-37 is encoded by the IL1F7 gene that undergoes alternative splicing, which results in the expression of five different isoforms of IL-37. IL1F7a (isoform 5, IL-37a) uses a unique start codon in exon 3 (prodomain), which is then spliced in exon 4 to 6 (forming the putative 12 β-strand-containing protein structure). IL1F7b (isoform 1, IL-37b) encodes the longest transcript variant, composed of exons 1 and 2 (prodomain) and exons 4 to 6. IL1F7c (isoform 4, IL-37c) is a transcript variant encompassing exons 1 and (prodomain) followed by exons 5 and 6. IL1F7d (isoform 2, IL-37d) has a prodomain limited to exon 1 (exon 2 is missing) followed by the complete IL-1-like sequence encoded by exons 4 to 6. IL1F7e (isoform 3, IL-37e) is only composed of exon 1, 5, and 6. IL-37b is the best characterized IL-37 isoform and has been shown to suppress the production of soluble TNF-α, IL-6, MIP-2, and of cell-associated IL-1α in IL-37b-overexpressing cells in response to LPS (Sharma, et al. (2008) *J. Immunol.* 180:5477). Further, the in vivo effect of IL-37b has been examined in IL-37b transgenic (tg) mice, wherein sublethal endotoxic shock was significantly decreased in IL-37b-tg mice as compared to normal littermates, in terms of hypothermia, metabolic acidosis, dehydration, rise in potassium concentration, and liver damage (Hold, et al. (2010) *Nat. Immunol.* 11:1014). In addition, levels of inflammatory cytokines (IL-6, IL-1β, IL-17, IFN-γ, etc.) are dampened in IL-37b-tg mice in response to LPS challenge (Nold, et al. (2010) *Nat. Immunol.* 11:1014). In an experimental model of intestinal bowel disease (dextran sodium sulfate-induced colitis), the severity of the intestinal inflammation is significantly lower in IL-37b-tg mice as compared to wild-type controls (McNamee, et al. (2011) *Proc. Natl. Acad. Sci. USA* 108:16711-6). Exemplary IL-37 proteins of use in this invention include, e.g., human IL-37a available under GENBANK Accession No. NP_775297; human IL-37b available under GENBANK Accession No. NP_055254; human IL-37c available under GENBANK Accession No. NP_775296; human IL-37d available under GENBANK Accession No. NP_775294 and human. IL-37d available under GENBANK Accession No. NP_775295.

IL-27 is a heterodimeric protein composed of EBI3 (also known as IL-27β) and IL-27α (also known as IL-30 or IL-27p28) (Pflanz, et al. (2002) *Immunity* 16:779-790), which signals through the IL27 receptor complex formed by WSX-1 and gp130 subunits. IL-27 has been shown to inhibit the Th17 response during inflammation (Stumhofer, et al. (2006) *Nat. Immunol.* 7:937-945; Batten, et al. (2006) *Nat. Immunol.* 7:929-936; Colgan & Rothman (2006) *Nat. Immunol.* 7:899-901), which contributes to the development of autoimmune inflammation in multiple sclerosis and rheumatoid arthritis. Consistent with the ability of IL-27 to decrease Th17 responses, continual delivery of IL-27 significantly suppresses the establishment of clinical disease in EAE, associated with a decreased proportion of Th17 cells in the CNS (Fitzgerald, et al. (2007) *J. Immunol.* 179:3268-3275). In addition, it has been found that IL-27 can also promote IL-10 synthesis by CD4$^+$ and CD8$^+$ T cells (Stumhofer, et al. (2007) *Nat. Immunol.* 8:1363-71; Fitzgerald, et al. (2007) *Nat. Immunol.* 8(12):1372-9; Awasthi, et al. (2007) *Nat. Immunol.* 8(12):1380-9). An exemplary IL-27 protein of use in this invention can be prepared using, e.g., human IL-27α available under GENBANK Accession No. NP_663634, and EBI3 available under GENBANK Accession No. NP_005755. The IL-27α and EBI3 proteins of IL-27 can be expressed as separate proteins or as a single chain protein. When expressed as a single chain protein, the IL-27α and EBI3 proteins can be directly fused to one another as a contiguous protein sequence or fused together via a linker, e.g., (GGGS)$_4$ (SEQ ID NO:1).

IL-13 is implicated as a key player in allergic disease. IL-13 induces immunoglobulin (Ig) class switching to IgE (Punnonen & de Vries (1994) *J. Immunol.* 152:1094-1102) and upregulate vascular cell adhesion molecule (VCAM)-1 expression (Bochner, et al. (1995) *J. Immunol.* 154:799-803). However, actions of IL-13 consistent with an anti-inflammatory role have been indicated by its activity in several systems. In particular, IL-13 inhibits IL-1, TNF-α, and nitric oxide synthesis but increases IL-1 receptor antagonist production (Hart, et al. (1989) *Proc. Nat. Acad. Sci. USA* 86(10):3803-7; Minty, et al. (1993) *Nature* 361:248-250; De Wall, et al. (1993) *J. Immunol.* 151:6370-6381; Yanagawa, et al. (1995) *Am. J. Respir. Cell Mol. Biol.* 12:71-76; Berkman, et al. (1996) *Immunology* 89:363-367). IL-13 inhibits chemokine synthesis by vascular endothelial and airway smooth-muscle cells (Marfaing-Koka, et al. (1995) *J. Immunol.* 154:1870-1878; John, et al. (1997) *J. Immunol.* 158:1841-1847; John, et al. (1998) *Am. J. Respir. Cell Mol. Biol.* 18:84-90). In vivo, IL-13 has been shown to inhibit TNF-α release, neutrophil accumulation, and TNF-α production in rat lung immune complex injury (Mulligan, et al. (1997) *J. Immunol.* 159:3483-3489), and endotoxin-induced lethality and increased serum TNF-α in the mouse (Di Santo, et al. (1997) *J. Immunol.* 159:379-382; Nicoletti, et al. (1997) *Eur. J. Immunol.* 27:1580-1583; Baumhofer, et al. (1998) *Eur. J. Immunol.* 28:610-615). Furthermore, in osteoarthritis synovial membrane treated with LPS, IL-13 inhibits the synthesis of IL-1β, TNF-α and stromelysin-1, reduces the level of IL-1β mRNA and stimulates the level of IL-1Ra mRNA (Jovanovic, et al. (1998) *Osteoarthritis Cartilage* 6(1):40-9). Therefore, IL-13 reduces the production of proinflammatory cytokines and metalloproteases, and favors the production of IL-1Ra. Exemplary IL-13 proteins of use in this invention include, e.g., human IL-13 available under GENBANK Accession Nos. NP_002179.

IL-1ra is a naturally occurring inhibitor of IL-1 (Arend (1993) *Adv. Immunol.* 54:167-227). IL-1ra is produced by a variety of cells including macrophages, fibroblasts, and keratinocytes (Arend, et al. (1985) *J. Immunol.* 134:3668-3875). IL-1ra binds to IL-1 receptor I on the cell surface but fails to trigger signal transduction, thereby acting as a competitive inhibitor of IL-1 binding to target cells (Dripps, et al. (1991) *J. Biol. Chem.* 266:10331-6). In inflammatory bowel disease, severe cases are associated with a decrease in IL-1ra leading to an imbalance of IL-1ra and IL-1 (Casini-Raggi, et al. (1995) *J. Immunol.* 154:2434-2440). The decrease of the IL-1ra:IL-1 ratio has been shown to account for acute cases of Crohn's disease and ulcerative colitis (Andus, et al. (1997) *Gut* 41:651-7; Heresbach, et al. (1997) *Am. J. Gastroenterol.* 92:1164-9). In the rabbit ligated-loop model of *Shigella* infection, administration of IL-1ra reduces intestinal inflammation (Perdomo, et al. (1994) *J. Exp. Med.* 180:1307-19), indicating that the imbalance between IL-1 and IL-1ra accounts for disease severity (Arondel, et al. (1999) *Infect. Immun.* 67:6056-6066). Further, in animal models of osteoarthritis (OA), IL-1 blockade by IL-1Ra has been shown to slow the progression of disease by blocking PGE$_2$ synthesis, collagenase and nitric oxide (NO) production by chondrocytes, and cartilage matrix degradation (Martel-Pelletier, et al. (1999) *Front. Biosci.*

4:D694-703; Caron, et al. (1996) *Arthritis Rheum.* 39:1535-44). In addition, in patients with rheumatoid arthritis, IL-1ra injected subcutaneously daily demonstrates a disease-modifying antirheumatic effect (Bresnihan (2002) *Clin. Exp. Rheumatol.* 20:S32-S34). Exemplary IL-1ra proteins of use in this invention include, e.g., human IL-1ra available under GENBANK Accession Nos. NP_000568, NP_776213 or NP_776214, as well as the IL-1ra protein used in Anakinra, which is a 153 amino acid residue, recombinant human IL-1ra that differs from native human IL-1ra by the addition of a single methionine residue on its amino terminus.

IFN-β down-regulates the expression of IL-1β and TNF-α and enhances IL-10 and IL-1 receptor antagonist production by lymphocytes in vitro (Tak, et al. (1999) Rheumatology (Oxford) 38:362-369; Rep, et al. (1996) *J. Neuroimmunol.* 67:111-118; Rep, et al. (1999) *J. Neuroimmunol.* 96:92-100), increases IL-1 receptor antagonist production by fibroblast-like synoviocytes (Palmer, et al. (2004) *Ann. Rheum. Dis.* 63:43-49), inhibits T-cell proliferation and migration, and prevents contact-dependent T-cell activation of monocytes (Jungo, et al. (2001) *Cytokine* 14:272-282). IFN-β also suppresses IFN-γ production and MHC class II expression by activated peripheral blood mononuclear cells (Yong, et al. (1998) *Neurology* 51:682-689). Further, studies have also found that IFN-β enhances expression of TGF-β1 and TGF-β1 receptor type II by peripheral blood mononuclear cells (Ossege, et al. (2001) *Int. Immunopharmacol.* 1:1085-1100). IFN-β has shown therapeutic promise as an anti-inflammatory cytokine in multiple sclerosis (Li, et al. (1999) *Ann. Neurol.* 46:197-206) and in reducing inflammation and slowing cartilage destruction in CIA (van Holten, et al. (2004) *Arthritis Res. Ther.* 6(3):R239-49). In addition, in vivo data from Lewis rats with EAE have shown IFN-β-induced down-regulation of critical adhesion molecules such as ICAM-1 and monocyte VLA-4 that clearly play a role in the pathogenesis of multiple sclerosis by controlling cellular trafficking within the CNS (Ruuls & Sedgwick (1998) *Immunol. Cell Biol.* 76:65-73). Exemplary IFN-β proteins of use in this invention include, e.g., human IFN-β available under GENBANK Accession No. NP_002167, as well as the IFNβ-1b protein used in Betaferon®/Betaseron® or Extavia®, and IFNβ-1α protein used in Avonex® or Rebif®.

TGF-β antagonizes the activation of important target genes of pro-inflammatory stimuli of NF-κB in macrophages and lymphocytes, such as inducible nitric oxide synthetase (iNOS) and MHC class I and class II antigens (Geiser, et al. (1993) *Proc. Natl. Acad. Sci.* 90:9944-9948; Vodovotz, et al. (1996) *J. Exp. Med.* 183:2337-2342). In addition, TGF-β decreases the expression of Type I and II IL-1 receptors and upregulates IL-1ra (Turner, et al. (1991) *Euro. J. Immunol.* 21:1635-39; Dubois, et al. (1990) *J. Exp. Med.* 172:737-744). Applied in the animal model EAE, TGF-β delays disease development and decreases the rate of recurrence in established disease (Kuruvilla, et al. (19910) *Proc. Natl. Acad. Sci. USA* 88:18-21). Further, in CIA, TGF-β decreases antibody production and alters histopathology with decreased lining membrane hyperplasia and limited mononuclear cell infiltration (Kuruvilla, et al. (19910) *Proc. Natl. Acad. Sci. USA* 88:18-21). Exemplary TGF-β proteins of use in this invention include, e.g., human TGF-β1 available under GENBANK Accession No. NP_000651.

Viral IL-10 proteins are functional orthologues of cIL-10, which have been found thus far in the Herpesviridae, Alloherpesviridae and Poxviridae families of viruses. Viral IL-10 proteins have been found to inhibit PBMC proliferation and production of proinflammatory cytokines IL-1α, IL-6, granulocyte-macrophage colony-stimulating factor, and TNF-α in lipopolysaccharide (LPS)-treated PMBC and monocytes (Spencer, et al. (2008) *Virology* 374:164-9; de Waal, et al. (1991) *J. Exp. Med.* 174:1209-1220; Hsu, et al. (1990) *Science* 250:830-2; Hsu, et al. (1992) *Int. Immunol.* 4:563-9; Vieira, et al. (1991) *Proc. Natl. Acad. Sci. USA* 88:1172-6) and reduce the levels of transcription of components of the MHC class II biosynthesis pathway (Spencer, et al. (2008) *Virology* 374:164-9; Jenkins, et al. (2008) *J. Virol.* 82:3736-50; de Waal, et al. (1991) *J. Exp. Med.* 174:915-24). However, the viral cytokine had not retained all properties of cIL-10. While human and murine IL-10 costimulate mouse thymocyte proliferation and mast cell proliferation and promote upregulation of MHC class II surface expression on B cells, Epstein-Barr virus (ebv) IL-10 lacks these functions (Go, et al. (1990) *J. Exp. Med.* 172:1625-31; MacNeil, et al. (1990) *J. Immunol.* 145:4167-73; Vieira, et al. (1991) *Proc. Natl. Acad. Sci. USA* 88:1172-6). Further examination has also revealed that the ability to inhibit IL-2 production by a CD4 T-cell clone is greatly reduced in comparison with that of the cIL-10s and that ebvIL-10 has an approximately 1,000-fold-lower affinity for the cellular IL-10R than hIL-10 (Liu, et al. (1997) *J. Immunol.* 152:1821-9). In particular, ebvIL-10 has been shown to be effective in inhibiting CIA (Keravala, et al. (2006) *Arthritis Res. Ther.* 8:R91; Kim, et al. (2000) *J. Immunol.* 164:1576-81; Ma, et al. (1998) *J. Immunol.* 161:1516-24), suppressing autoimmune diabetes (Yang, et al. (2002) *J. Immunol.* 168:6479-85), ameliorating symptoms of necrotizing pancreatitis (Minter, et al. (2001) *J. Immunol.* 167:1053-9), and improving survival of sepsis (Oberholzer, et al. (2001) *Proc. Natl. Acad. Sci. USA* 98:11503-8). Exemplary viral IL-10 proteins of use in this invention include, e.g., Human herpes 5 IL-10/UL111A (GENBANK Accession No. AAR31656, AAF36285, or YP_081552), Human herpesvirus 5 latency associated cmvIL-10 (GENBANK Accession No. ACR49217), Rhesus cytomegalovirus UL111A/vIL-10 (GENBANK Accession No. AF200417), African green monkey cytomegalovirus vIL-10 (GENBANK Accession No. AAF63435, Baboon cytomegalovirus IL-10-like protein (GENBANK Accession No. AAF63436), Epstein-Barr virus protein BCRF1 (GENBANK Accession No. CAD53385 or P03180), Rhesus lymphocryptovirus BCFR1 (GENBANK Accession No. AAK95412), Baboon lymphocryptovirus IL-10 (GENBANK Accession No. AAF23949), Equine herpesvirus 2 IL-10 (GENBANK Accession No. AAB26148), Ovine herpesvirus 2 IL-10 (GENBANK Accession No. ABB22222), Koi herpesvirus IL-10 (GENBANK Accession No. YP_001096169), Orf virus IL-10 (GENBANK Accession No. AAC57332), Pan paniscus viral IL-10 homolog (GENBANK Accession No. XP 003804206), Sheeppox virus IL-10 (GENBANK Accession No. NP_659579), Goatpox virus IL-10 (GENBANK Accession No. YP_001293197) and Lumpy skin disease virus IL-10 (GENBANK Accession No. AAN02729). See also, Slobedman, et al. (2009) *J. Virol.* 83:9618-29.

Helminth C-type lectins, sharing sequence and structural similarity with mammalian immune cell lectins, have been identified from nematode parasites and shown to exert profound anti-inflammatory effects on the host immune system (Pritchard, et al. (1994) *Int. J. Parasitol.* 24:495-500; Holland, et al. (2000) *Eur. J. Immunol.* 30:1977-87; Balic, et al. (2004) *Eur. J. Immunol.* 34:3407-59). Exemplary helminth C-type lectins of use in this invention include, e.g., *Heligmosomoides polygyrus* C-type lectin-1 (GENBANK Accession No. FJ456978) and *Nippostrongylus brasiliensis* C-type lectin-2 (GENBANK Accession No. ACS37723).

Other anti-inflammatory and immunosuppressant proteins of use in the invention include, e.g., Glucocorticoid-induced leucine zipper (GILZ), a protein which interacts with and inhibits the function of NFκB and AP-1 (Ayroldi & Riccardi (2009) *FASEB J.* 23:3649-3658); annexin AI (AnxAl) and its mimetic peptides (e.g., Ac2-26), which reduce the production of inflammatory mediators such as TNF-α, IL-1β, IL-6, and NO (Perretti & D'Acquisto (2009) *Nat. Rev. Immunol.* 9:62-70; Girol, et al. (2013) *J. Immunol.* 190:5689-5701); IL-18 binding protein from vaccinia virus, cowpox virus or *Molluscum contagiosum* virus, which blocks the effects of IL-18 (Smith, et al. (2000) *J. Gen. Virol.* 81:1223-30); the vaccinia virus IFN-α binding protein (Colamonici, et al. (1995) *J. Biol. Chem.* 270:15974-8); and viral serpins (Chen, et al. (2011) *Methods Enzymol.* 499:301-29).

It is also to be understood that by any particular gene/protein, the invention encompasses the gene/protein and any obvious variants thereby, which may be allelic variants or other modifications, which maintain the immunosuppressive and/or anti-inflammatory activities. The present invention also includes families of the gene/protein, which are related by sequence similarity or function.

A chimeric antigen receptor, also known as a CAR, artificial T cell receptor, chimeric T cell receptor, or chimeric immunoreceptor, of this invention is a fusion protein composed of at least one antigen targeting domain or recognition domain, a transmembrane region that anchors the antigen targeting domain to the cell surface, at least one signaling endodomain and an optional extracellular spacer/hinge domain between the antigen targeting domain or recognition domain and transmembrane region.

Antigen targeting or antigen recognition by CAR molecules can involve the use of a single chain variable fragment (scFv) that has been assembled from a monoclonal antibody. Alternatively, targeting moieties can include receptors such as NKG2D, NKp30 or dectin1 (Zhang & Sentman (2013) *J. Immunol.* 190:2455-63; Zhang, et al. (2012) *J. Immunol.* 189:2290-9); ligands (Altenschmidt, et al. (1996) *Clin. Cancer Res.* 2:1001-8; Muniappan, et al. (2000) *Cancer Gene Ther.* 7:128-134), peptides (Pameijer, et al. (2007) *Cancer Gene Ther.* 14:91-97), chimeric ligands (Davies, et al. (2012) *Mol. Med.* 18:565-576), receptor derivatives (Scholler, et al. (2012) *Sci. Translation. Med.* 4: Article IDS 132ra53; Zhang, et al. (2012) *J. Immunol.* 189:2290-9), and single domain antibodies (Sharifzadeh, et al. (2012) *Cancer Res.* 72:1844-52). When two or more antigen-specific targeting domains target at least two different antigens, the domains may be arranged in tandem and separated by linker sequences. In other embodiments, the extracellular spacer domain is optional.

Antigens or ligands, which can be used as targets at a site of inflammation or autoimmunity, include molecules specific for inflammatory diseases or autoimmune diseases, as well as tissue- or cell-specific molecules. Examples of antigens or ligands specific for inflammatory diseases or autoimmune diseases, which may be targeted by the CARs of the invention include, but are not limited to, one or more of the antigens listed in Table 1.

TABLE 1

| Disease or Condition | Target |
| --- | --- |
| Inflammatory bowel disease (IBD) | Antigen or ligand expressed in diseased colon or ileum |

TABLE 1-continued

| Disease or Condition | Target |
| --- | --- |
| Rheumatoid arthritis | Antigen or ligand is an epitope of collagen or an antigen present in joints, e.g., Rheumatoid factor IgG complexes |
| Type I diabetes mellitus or autoimmune insulitis | Pancreatic β cell antigen and/or insulin |
| Multiple sclerosis | A myelin basic protein (MBP) antigen or MOG-I or MOG2-2, proteolipid protein, myelin oligodendrocyte glycoprotein and/or a neuronal antigen |
| Autoimmune uveitis or uveoretinitis | S-antigen or another uveal or retinal antigen |
| Autoimmune orchitis | Testicular antigen |
| Autoimmune oophoritis | An ovarian antigen |
| Psoriasis | Keratinocyte antigen or another antigen present in dermis or epidermis |
| Vitiligo | Melanocyte antigen such as melanin or tyrosinase |
| Autoimmune prostatitis | Prostate antigen |
| Autoimmune hemolytic anemia | Rh blood group antigen |
| Autoimmune thrombocytopenic purpura | Platelet integrin GpIIb:IIIa |
| Goodpasture's syndrome | Noncollagenous domain of basement membrane collagen type IV |
| Pemphigus vulgaris | Epidermal cadherin |
| Graves' Disease | Thyroid Peroxidase and/or thyroid-stimulating hormone receptor |
| Hashimoto Thyroiditis | Thyroglobulin |
| Systemic Vasculitides | Myeloperoxidase |
| Crohn's Disease | Glycoprotein 2 |
| Primary Biliary Cirrhosis | M2 or components thereof (e.g., BCOADC-E2, OGDC-E2, PDC-E2), Sp100, Gp210 and/or Nup62 |
| Autoimmune Hepatitis II | Formiminotransferase Cyclodeaminase and/or Cytochrome P450 2D6 |
| Celiac Disease | Tissue transglutaminase and/or gliadin |
| Thromboembolic Syndrome | β2 Glycoprotein I |
| Systemic Vasculitides/ Wegener's Granulomatosis | Proteinase 3 |

When targeting an inflammatory response, the target of the CAR of the invention can be an antigen expressed on or by a dendritic cell, macrophage/monocyte, granulocyte or eosinophil present at the inflammation site. Such antigens include, but are not limited to, AOC3 (VAP-1), CCL11 (eotaxin-1), CD20, CD3, CD4, CD5, IFN-γ, IgE, IgE Fc region, IL-1, IL-12, IL-23, IL-17, IL-17A, IL-22, IL-6, integrin α4β7, LFA-1 (CD1 la), OX-40L, and TNF-α.

When targeting particular tissues or cells, the target of the CAR of the invention can be a biomarker or cell ligand including, but not limited to, those listed in Table 2.

TABLE 2

| Tissue | Biomarker/Cell Ligand |
| --- | --- |
| Lung[a] | FGFR2 |
| | Sprouty Homolog 2 (SPRY2) |
| | Stimulated by retinoic acid 6 (STRA6) |
| | CD68 |
| | Mucin 1 |
| | Bone morphogenetic Protein Receptor Type 1A |
| Neuron[a] | S-100 protein |
| Cardiovascular System | Caveolin 1 |

TABLE 2-continued

| Tissue | Biomarker/Cell Ligand |
|---|---|
| Liver[a] | SLCO1B1 |
| | CYP1A2 |
| | CYP3A4 |
| Kidney[a] | Glomeruli (NPHS2) |
| Neurons (CNS)[a] | Myelin Basic Protein |
| | Myelin Oligodendrocyte Glycoprotein |
| | Proteolipid Protein |
| Glial cells (CNS)[a] | Aquaporin-4 (AQP4) |
| Heart[a] | β-adrenergic receptor |
| Pancreas/Islet Cells[b] | Retinoic acid early inducible (RAE)-1 |
| minor salivary glands[c] | B7H6 |
| Liver (bile duct epithelial cells)[a] | Carbonic anhydrase IX (CIAX) |
| CNS[a] | Mutant Superoxide dismutase (SOD)-1 |
| Inflammatory tissues[a] | Autoimmune TCRs |
| Inflammatory tissues[d] | MHCI/II + Autoimmune peptide |

[a]ScFv as antigen-specific targeting domain;
[b]NKG2D as antigen-specific targeting domain;
[c]NKp30 as antigen-specific targeting domain;
[d]Autoimmune TCR as antigen-specific targeting domain.

Exemplary antigen-specific targeting domains of the instant CAR include, but are not limited to, Cam-3001, CD125, CD154, CD2, CD23 (IgE receptor), CD25 (a chain of IL-2 receptor), IL-6 receptor, rhuMAb β7 and OX-40.

In addition to antigen-specific approaches, two "universal" CAR systems have been described. These generic CARs containing avidin (Urbanska, et al. (2012) *Cancer Res.* 72:1844-52) or antifluorescein isothiocyanate (FITC) scFv (Ang, et al. (2011) *Mol. Ther.* 19: abstract 353; Chmielewski, et al. (2004) *J. Immunol.* 173:7647-7653), enabling their use in conjunction with separate targeting moieties that have been biotinylated or conjugated to FITC, respectively.

In embodiments wherein the antigen targeting domain is a scFv, the scFv can be derived from the variable heavy chain (VH) and variable light chain (VL) regions of an antigen-specific mAb linked by a flexible linker. The scFv retains the same specificity as the full antibody from which it was derived (Muniappan, et al. (2000) *Cancer Gene Ther.* 7:128-134). Various methods for preparing an scFv can be used including methods described in U.S. Pat. No. 4,694,778; Bird, et al. (1988) *Science* 242:423-442; Ward, et al. (1989) *Nature* 334:54454; and Skerra, et al. (1988) *Science* 242:1038-1041. In certain embodiments, the scFv is humanized or is a fully human scFv.

As indicated, the CAR of the invention may also have an extracellular spacer/hinge domain and a transmembrane region or domain. The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, a CD3ζ chain, CD28, CD3ε, CD45, CD4, CD5, CD7, CD8, CD9, CD16, CD22, CD33, CD37, CD64, CD80, CD86, CD134, CD137, ICOS, CD154, H2-Kb, FcεRIγ or a GITR can be used. See, e.g., Kahlon, et al. (2004) *Cancer Res.* 64:9160-9166; Schambach, et al. (2009) *Methods Mol. Biol.* 506:191-205; Jensen, et al. (1998) *Biol. Blood Marrow Transplant* 4:75-83; Patel, et al. (1999) *Gene Ther.* 6:412; Song, et al. (2012) *Blood* 119:696-706; Carpenito, et al. (2009) *Proc. Natl. Acad. Sci. USA* 106:3360-5; Hombach, et al. (2012) *Oncoimmunology* 1:458-66) and Geiger, et al. (2001) *Blood* 98:2364-71. The artificially designed transmembrane domain is a polypeptide mainly composed hydrophobic residues such as leucine and valine. It is preferable that a triplet of phenylalanine, tryptophan and valine is found at each end of the synthetic transmembrane domain. See, U.S. Pat. No. 7,052,906. In one embodiment, the transmembrane domain is composed of residues 153 to 180 of CD28 (GENBANK Accession No. NP_006130). As another embodiment, the transmembrane domain is composed of residues 162 to 183 of a GITR (GENBANK Accession No. NP_004186).

In the CAR of the invention, a spacer or hinge domain can be arranged between the extracellular antigen targeting domain and the transmembrane domain, and/or between the intracellular signaling endodomain and the transmembrane domain. A spacer domain refers to any oligopeptide or polypeptide that serves to link the transmembrane domain with the antigen targeting domain and/or the transmembrane domain with the intracellular signaling endodomain. The spacer domain can be up to 300 amino acids, preferably 10 to 100 amino acids, 25 to 50 amino acids or 2 to 10 amino acids in length.

The spacer domain preferably has a sequence that promotes binding of a CAR with an antigen and enhances signaling in a cell. Examples of an amino acid that is expected to promote the binding include cysteine, a charged amino acid, and serine and threonine in a potential glycosylation site, and these amino acids can be used as an amino acid constituting the spacer domain.

As the spacer domain, all or a part of residues 118 to 178 of CD8α (GENBANK Accession No. NP_001759.3), residues 135 to 195 of CD8β (GENBANK Accession No. AAA35664), residues 315 to 396 of CD4 (GENBANK Accession No. NP_000607.1), or residues 137 to 152 of CD28 (GENBANK Accession No. NP_006130.1) can be used. Also, as the spacer domain, a part of a constant region of an antibody H chain or L chain (CH1 region or CL region) can be used. Further, the spacer domain may be an artificially synthesized sequence.

The intracellular signaling endodomain used in this invention is a molecule that can transmit a signal into a cell when the extracellular antigen targeting domain present within the same molecule binds to (interacts with) an antigen. Natural T cell-activation is transmitted by two different kinds of cytoplasmic signaling endodomain, that is, a sequence for initiating antigen-dependent primary activation via a TCR complex (primary cytoplasmic signaling endodomain) and a sequence for acting antigen-independently to provide a secondary or costimulating signal (secondary cytoplasmic signaling endodomain or costimulatory endodomain). Therefore, while some embodiments embrace a CAR with only a primary cytoplasmic signaling endodomain, in other embodiments, a CAR of the invention includes a primary signaling endodomain and a secondary cytoplasmic signaling endodomain.

The primary cytoplasmic signaling endodomain regulates primary activation of a TCR complex. The primary cytoplasmic signaling sequence that stimulates the activation may include a signal transduction motif known as an immunoreceptor tyrosine-based activation motif (ITAM) (Asp/Glu)-Xaa-Xaa-Tyr*-Xaa-Xaa-(Ile/Leu)-Xaa$_{6-8}$-Tyr*-Xaa-Xaa-(Ile/Leu) (SEQ ID NO:2) (Reth, et al. (1989) *Nature* 338:383-384).

Examples of proteins having an ITAM that can be used in the present invention include CD3ζ, FcRγ, FcRβ, CD3γ, CD3δ, CD3ε, CD5, CD22, CD79a, CD79b, and CD66d. Specifically, examples of the ITAM include residues 51 to 164 of CD3ζ (GENBANK Accession No. NP_932170), residues 45 to 86 of FcεRIγ (GENBANK Accession No. NP_004097), residues 201 to 244 of FcεRIβ (GENBANK Accession No. NP_000130), residues 139 to 182 of CD3γ (GENBANK Accession No. NP_000064), residues 128 to 171 of CD3δ (GENBANK Accession No. NP_000723), residues 153 to 207 of CD3ε (GENBANK Accession No. NP_000724), residues 402 to 495 of CD5 (GENBANK Accession No. NP_055022), residues 707 to 847 of CD22 (GENBANK Accession No. NP_001762), residues 166 to 226 of CD79a (GENBANK Accession No. NP_001774), residues 182 to 229 of CD79b (GENBANK Accession No. NP_000611), and residues 177 to 252 of CD66d (GENBANK Accession No. NP_001806), and their variants having the same function as these peptides have. The referenced residues are based on amino acid sequence information from GENBANK and is based on the full length of the precursor (including a signal peptide sequence etc.) of each protein.

Examples of secondary cytoplasmic signaling endodomains or costimulatory endodomains that can be used in the present invention include sequences derived from CD2, CD4, CD5, CD8α, CD8β, CD28, CD134, CD137, ICOS, CD122, CD132, Dap10, Dap12, CD40 and CD154. Specific examples thereof include residues 236 to 351 of CD2 (GENBANK Accession No. NP_001758), residues 421 to 458 of CD4 (GENBANK Accession No. NP_000607), residues 402 to 495 of CD5 (GENBANK Accession No. NP_055022), residues 207 to 235 of CD8α (GENBANK Accession No. NP_001759), residues 196 to 210 of CD83 (GENBANK Accession No. AAA35664), residues 181 to 220 of CD28 (GENBANK Accession No. NP_006130), residues 214 to 255 of CD137 (4-1BB, GENBANK Accession No. NP_001552), residues 241 to 277 of CD134 (OX40, GENBANK Accession No. NP_003318), and residues 166 to 199 of ICOS (GENBANK Accession No. NP_036224), and their variants having the same function as these peptides have. In some embodiments, the costimulatory endodomain is from CD28, 41BB, OX40, ICOS, or a combination thereof.

While any suitable endodomain can be used in the CAR of the invention, in certain embodiments, the invention embraces the use of all or a part of the endodomains of CD28 and CD3. In specific embodiments, intracellular signaling endodomains are those of the T cell antigen receptor complex, e.g., CD28, DAP10, CD137, CD2, which are used either alone or in a series with CD3ζ. One or multiple endodomains may be employed, as so-called third generation CARs have at least 2 or 3 signaling domains fused together for additive or synergistic effect, for example.

In a CAR containing more than one intracellular endodomain, an oligopeptide linker or a polypeptide linker can be inserted between the intracellular endodomains to link the domains. Preferably, a linker having a length of 2 to 10 amino acids can be used. Particularly, a linker having a glycine-serine continuous sequence can be used.

In addition to the antigen targeting domain, optional extracellular spacer/hinge domain, transmembrane domain, and signaling endodomain, the CAR of the invention can also include a signal peptide sequence linked to the N-terminus of the CAR. Signal peptide sequences exist at the N-terminus of many secretory proteins and membrane proteins, and have a length of 15 to 30 amino acids. Since many of the protein molecules mentioned above have signal peptide sequences, these signal peptides can be used as a signal peptide for the CAR of this invention.

As will be appreciated by one of skill in the art, in some instances, a few amino acids at the ends of the antigen targeting domain can be deleted, usually not more than 10, more usually not more than 5 residues. Also, it may be desirable to introduce a small number of amino acids at the borders, usually not more than 10, more usually not more than 5 residues. The deletion or insertion of amino acids will usually be as a result of the needs of the construction, providing for convenient restriction sites, ease of manipulation, improvement in levels of expression, or the like. In addition, the substitute of one or more amino acids with a different amino acid can occur for similar reasons, usually not substituting more than about five amino acids in any one domain.

For the purposes of this invention, "nucleic acids" refer to single or double stranded nucleic acid molecules, which are isolated and provided in the form of RNA, a complementary polynucleotide (cDNA), a genomic polynucleotide and/or a composite polynucleotide (e.g., a combination of the above). As used herein, the term "nucleic acid construct" refers to a nucleic acid molecule, which includes nucleic acids encoding a CAR and nucleic acids encoding an anti-inflammatory or immunosuppressant protein. In some embodiments, the nucleic acid construct is a linear naked molecule or a vector, e.g., a plasmid, a bacmid, a phagemid, a cosmid, a phage, a virus or an artificial chromosome.

In accordance with the present invention, the nucleic acid construct is transformed or introduced into an immune cell and is transcribed and translated to produce a product (e.g., a chimeric receptor, anti-inflammatory or immunosuppressant protein, and optionally a suicide protein). Thus, the nucleic acid construct further includes at least one promoter for directing transcription of the CAR and anti-inflammatory or immunosuppressant protein. According to some embodiments, nucleic acids encoding the CAR and anti-inflammatory or immunosuppressant protein are operably linked to at least one promoter sequence. A coding nucleic acid is "operably linked" to a regulatory sequence (e.g., promoter) if the regulatory sequence is capable of exerting a regulatory effect on the coding sequence linked thereto.

In the nucleic acid construct of the invention, at least one promoter directs transcription of the CAR and anti-inflammatory or immunosuppressant protein. According to some embodiments, nucleic acids encoding the CAR and anti-inflammatory or immunosuppressant protein are independently expressed via different promoters, i.e., nucleic acids encoding the CAR are operably linked to a first promoter and nucleic acids encoding the anti-inflammatory or immunosuppressant protein are operably linked to a second promoter, which may be the same or different than the first promoter. In accordance with particular embodiments, expression of the anti-inflammatory or immunosuppressant protein by the second promoter is enhanced by CAR signaling. In this respect, CAR binding to a ligand expressed preferentially at the site of tissue damage will activate expression of the anti-inflammatory or immunosuppressant protein in a location specific manner and dampen inflammation at that site. Examples of promoter elements that are responsive to CAR signaling include, but are not limited to, the nuclear factor of activated T-cells (NFAT)-responsive promoter (Zhang, et al. (2011) *Mol. Ther.* 19:751-759), viral LTR, EF1-alpha promoter, or a doxycycline-responsive promoter. While it is contemplated that a CAR and anti-inflammatory or immunosuppressant protein expressed via different promoters can be achieved using two independent nucleic acid constructs, in accordance with the present invention, it is preferable that the nucleic acids encoding the CAR and anti-inflammatory or immunosuppressant protein reside on a single nucleic acid construct.

According to certain embodiments of the invention, nucleic acids encoding the CAR and anti-inflammatory or immunosuppressant protein are co-expressed via a single promoter, i.e., nucleic acids encoding the CAR and nucleic acids encoding the anti-inflammatory or immunosuppressant protein are in tandem and operably linked to a single promoter. A coding nucleic acid is "operably linked" to a regulatory sequence (e.g., promoter) if the regulatory sequence is capable of exerting a regulatory effect on the coding sequence linked thereto. In other words, the promoter(s) of the invention is positioned so as to promote transcription of the messenger RNA from the DNA encoding the CAR and anti-inflammatory or immunosuppressant protein.

The promoter(s) of the invention can be of genomic origin or synthetically generated. A variety of promoters for use in T cells have been described in the art. For example, the CD4 promoter is disclosed by Marodon, et al. ((2003) *Blood* 101(9):3416-23). The promoter can be constitutive or inducible, where induction is associated with the specific cell type, a specific level of maturation, or drug (e.g., tetracycline or doxorubicin). Alternatively, a number of viral promoters are also suitable. Promoters of interest include the β-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The simultaneous or co-expression of a CAR and anti-inflammatory or immunosuppressant protein via a single promoter may be achieved by the use of an internal ribosomal entry site (IRES) or cis-acting hydrolase element. The term "internal ribosome entry site" or "IRES" defines a sequence motif that promotes attachment of ribosomes to that motif on internal mRNA sequences. Consequently, an mRNA containing an IRES sequence motif results in two translational products, one initiating from the 5'-end of the mRNA and the other by an internal translation mechanism mediated by the IRES. A number of IRES have been described and can be used in the nucleic acid construct of this invention. See, e.g., U.S. Pat. No. 8,192,984; WO 2010/119257; and US 2005/0112095.

A "cis-acting hydrolase element" or "CHYSEL" refers to a peptide sequence that causes a ribosome to release the growing polypeptide chain that it is being synthesizes without dissociation from the mRNA. In this respect, the ribosome continues translating and therefore produces a second polypeptide. Peptides such as the foot and mouth disease virus (FMDV) 2A sequence (GSGSRVTELLY-RMKRAETYC PRPLLAIHPTEAR-HKQKIVAPVKQLLNFDLLKLAGDVESNPGP, SEQ ID NO:3), sea urchin (*Strongylocentrotus purpuratus*) 2A sequence (DGFCILYLLLILLMRSGDVETNPGP, SEQ ID NO:4); Sponge (*Amphimedon queenslandica*) 2A sequence (LLCFMLLLLLSGDVELNPGP, SEQ ID NO:5; or HHFMFLLLLL AGDIELNPGP, SEQ ID NO:6); acorn worm (*Saccoglossus kowalevskii*) (WFLVLLSFILSGDI-EVNPGP, SEQ ID NO:7) 2A sequence; amphioxus (*Branchiostoma floridae*) (KNCAMYMLLLSGDVETNPGP, SEQ ID NO:8; or MVISQLMLKLAGDVEENPGP, SEQ ID NO:9) 2A sequence; porcine teschovirus-1 (GS-GATNFSLLKQAGDVEENPGP, SEQ ID NO:10) 2A sequence (P2A); *Thosea asigna* virus (GSGEGRGSLL TCGDVEENPGP, SEQ ID NO:11) 2A sequence (T2A); and equine rhinitis A virus (GSGQCTNYALLKLAGD-VESNPGP, SEQ ID NO:12) 2A sequence are CHYSELs of use in this invention. In some embodiments, the 2A sequence is a naturally occurring or synthetic sequence that includes the 2A consensus sequence D-X-E-X-NPGP (SEQ ID NO:13), in which X is any amino acid residue. In preferred embodiments, a furin sequence is included upstream of the 2A sequence to allow the proteins to be separated.

The sequence of the open reading frames encoding the CAR and anti-inflammatory or immunosuppressant protein can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA or provide T cell-specific expression (Barthel & Goldfeld (2003) *J. Immunol.* 171(7):3612-9). Also, it may be further advantageous to use endogenous or exogenous non-coding regions to stabilize the mRNA.

For expression of a CAR or anti-inflammatory or immunosuppressant protein, the naturally occurring or endogenous transcriptional initiation region of the nucleic acid sequence encoding N-terminal component of the CAR or anti-inflammatory or immunosuppressant protein can be used to generate the CAR or anti-inflammatory or immunosuppressant protein in the target host. Alternatively, an exogenous transcriptional initiation region can be used which allows for constitutive or inducible expression, wherein expression can be controlled depending upon the target host, the level of expression desired, the nature of the target host, and the like.

The termination region(s) of the construct may be provided by the naturally occurring or endogenous transcriptional termination regions of the nucleic acids encoding the C-terminal component of the last gene. Alternatively, the termination region may be derived from a different source. For the most part, the source of the termination region is generally not considered to be critical to the expression of a recombinant protein and a wide variety of termination regions can be employed without adversely affecting expression.

In some embodiments of the invention, a nucleic acid construct or cell harboring the nucleic acid construct includes a nucleic acid encoding a protein that is capable of triggering cell death or elimination. Examples of such proteins include suicide proteins such as thymidine kinase (TK) of the HSV virus (herpesvirus) type I (Bonini, et al. (1997) *Science* 276:1719-1724), a Fas-based "artificial suicide gene" (Thomis, et al. (2001) *Blood* 97:1249-1257), *E. coli* cytosine deaminase gene or caspase-9, which are activated by gancyclovir, AP1903, 5-fluorocytosine or a specific chemical inducer of dimerization (CID), respectively.

The nucleic acid encoding the protein for cell death or elimination is advantageously provided in the nucleic acid construct of the invention to allow for the opportunity to ablate the transduced immune cells in case of toxicity and to destroy the chimeric construct once the signs or symptoms of disease have been reduced or ameliorated. The use of suicide genes for eliminating transformed or transduced cells is described in the art. For example, Bonini, et al. ((1997) *Science* 276:1719-1724) teach that donor lymphocytes transduced with the HSV-TK suicide gene provide antitumor activity in patients for up to one year and elimination of the transduced cells is achieved using ganciclovir. Further, Gonzalez, et al. ((2004) *J. Gene Med.* 6:704-711)

describe the targeting of neuroblastoma with cytotoxic T lymphocyte clones genetically modified to express a chimeric scFvFc: ζ immunoreceptor specific for an epitope on L1-CAM, wherein the construct further expresses the hygromycin thymidine kinase (HyTK) suicide gene to eliminate the transgenic clones.

It is contemplated that the nucleic acid encoding the protein for cell death or elimination can be expressed from the same promoter as the CAR and/or anti-inflammatory or immunosuppressant protein or from a different promoter. Generally, however, nucleic acid encoding the protein for cell death or elimination, CAR and anti-inflammatory or immunosuppressant protein reside on the same construct or vector. Expression of the protein for cell death or elimination from the same promoter as the CAR and/or anti-inflammatory or immunosuppressant protein can be accomplished using the IRES or CHYSEL sequences described herein.

In certain embodiments of the invention, a nucleic acid construct or cell harboring the nucleic acid construct uses a detectable marker so that the cell that harbors the nucleic acid construct is identifiable, for example for qualitative and/or quantitative purposes. The detectable marker may be detectable by any suitable means in the art, including by flow cytometry, fluorescence, spectrophotometry, and so forth. An example of a detectable marker is one that encodes a nonfunctional gene product but that is still detectable by flow cytometry means, for example, or can be used to select transgenic cells by flow cytometry or magnetic selection. In addition to detection, the marker protein can be used as a means to eliminate the transduced cells in vivo via an antibody that recognizes the marker protein. Examples of marker proteins of use in cell elimination include, e.g., truncated CD19 (Tey, et al. (2007) *Biol. Blood Marrow Transplant* 13:913-24), the extracellular region of CD20 (Introna, et al. (2000) *Hum. Gene Ther.* 11:611-20; Griffioen, et al. (2009) *Haematologica* 94:1316-20), and the extracellular region of EGFR (Terakura, et al. (2012) *Blood* 119: 72-82). See also, Lang, et al. (2004) *Blood* 103:3982-5. Incorporation of these proteins into gene-modified T cells renders the cells susceptible to elimination by clinically used anti-CD19 antibodies, anti-CD20 antibodies, and anti-EGFR antibodies (e.g., cetuximab).

A nucleic acid construct according to the present invention can be produced by any means known in the art, though preferably it is produced using recombinant DNA techniques. Nucleic acids encoding the CAR can be prepared and assembled into a complete coding sequence by standard techniques of molecular cloning (genomic library screening, PCR, primer-assisted ligation, site-directed mutagenesis, etc.). Nucleic acids encoding the other moieties (e.g., anti-inflammatory or immunosuppressant protein, IRES or CHYSEL) may be similarly prepared. The resulting nucleic acids are preferably inserted into an expression vector and used to transform suitable mammalian host cells, preferably immune cells such as T lymphocyte cells.

The constructs and mammalian cells of this invention find application in subjects having or suspected of having an inflammatory condition, in particular a chronic inflammatory condition, or immune-mediated autoimmunity. Chronic inflammatory conditions and autoimmune diseases that can be treated using the immune cells and nucleic acid constructs of this invention include, for example, rheumatoid arthritis, reactive arthritis, multiple sclerosis, Type I diabetes mellitus or autoimmune insulitis, systemic lupus erythematosus, autoimmune uveoretinitis, autoimmune vasculitis, bullous pemphigus, myasthenia gravis, autoimmune thyroiditis or Hashimoto's disease, Sjogren's syndrome, granulomatous orchitis, autoimmune oophoritis, Inflammatory bowel disease, Crohn's disease, sarcoidosis, rheumatic carditis, ankylosing spondylitis, Grave's disease, Scleroderma, Amyotrophic Lateral Sclerosis, autoimmune hemolytic anemia, psoriasis, vitiligo, eczema, primary biliary cirrhosis, autoimmune prostatitis, Goodpasture's syndrome, autoimmune hepatitis II, celiac disease, ulcerative colitis, thromboembolic syndrome, systemic vasculitides/Wegener's granulomatosis, autoimmune thrombocytopenic purpura, arthritis deformans, Lyme disease arthritis, osteoarthritis, psoriatic arthritis, gout, fibromyalgia, Still's disease, chronic uveitis, chronic back or neck pain and sciatica, Addison's disease, Gaucher's disease, Huntington's disease, muscular dystrophy, cystic fibrosis and idiopathic pulmonary fibrosis. See, e.g., Paul, W. E. (1993) *Fundamental Immunology*, Third Edition, Raven Press, New York, Chapter 30, pp. 1033-1097; and Cohen, et al. (1994) *Autoimmune Disease Models, A Guidebook*, Academic Press, 1994.

Accordingly, the invention further relates to a method for treating inflammation, in particular chronic inflammation, or immune-mediated autoimmunity by delivering to a subject in need of treatment an immune cell of this invention. The step of delivering the immune cell to the subject generally involves introducing, e.g., via transduction, transposons or electroporation, a nucleic acid construct of the invention into an isolated immune cell (e.g., an autologous or third party-derived immune cell) and introducing into the subject the transduced/transformed immune cell, thereby effecting inflammatory or immunosuppressive responses in the subject to treat or ameliorate chronic inflammation or immune-mediated autoimmunity.

"Immune cell" as used herein refers to the cells of the mammalian immune system including but not limited to antigen presenting cells, B-cells, basophils, cytotoxic T-cells, dendritic cells, eosinophils, granulocytes, helper T-cells, leukocytes, lymphocytes, macrophages, mast cells, memory cells, monocytes, natural killer cells, neutrophils, phagocytes, plasma cells and T-cells (e.g., naive T cells, central memory T cells, effector memory T cells). In particular embodiments, the immune cell of the invention is a T cell. In certain embodiments, the T cell is a CD4+ T cell.

Suitable T cells that can be used include autologous T lymphocyte cells, third party-derived T cells, transformed tumor or xenogenic immunologic effector cells, tumor infiltrating lymphocytes, cytotoxic lymphocytes or other cells that are capable of producing effector proteins when activated. As is known to one of skill in the art, various methods are readily available for isolating these cells from a subject. For example, using cell surface marker expression or using commercially available kits (e.g., ISOCELL from Pierce, Rockford, Ill.).

It is contemplated that the nucleic acid construct can be introduced into the immune cells as naked DNA or in a suitable vector. Methods of stably transfecting immune cells by electroporation using naked DNA or capped mRNA are known in the art. See, e.g., U.S. Pat. No. 6,410,319. Naked DNA generally refers to the DNA encoding the nucleic acid construct of the invention contained in an expression vector in proper orientation for expression.

Alternatively, a viral vector (e.g., a retroviral vector, adenoviral vector, adeno-associated viral vector, or lentiviral vector) can be used to introduce the nucleic acid construct of the invention into immune cells. Suitable vectors for use in accordance with the method of the invention are non-replicating in the immune cells. A large number of vectors are known that are based on viruses, where the copy number of the virus maintained in the cell is low enough to maintain the viability of the cell. Illustrative vectors include the pFB-neo vectors (STRATAGENE), as well as vectors based on HIV, SV40, EBV, HSV or BPV.

Both lentiviruses and retroviruses have been widely used as gene transfer vectors, and they compose the vector system that is currently used in the majority of clinical gene therapy trials (Sinn, et al. (2005) *Gene Ther.* 12:1089-1098). However, the lentiviral vectors have some advantages because they mediate the efficient transduction of cells, can be used with both dividing and nondividing cells, result in long-term, stable transgene expression and appear to be less prone to gene silencing (Sinn, et al. (2005) *Gene Ther.* 12:1089-1098).

Nonviral gene transfer technologies have also been explored for gene therapy. One approach includes the electrotransfer of DNA plasmids using the Sleeping Beauty (SB) transposon/transposase system into primary human immune cells, which has been shown to provide efficient and stable CD19-specific CAR gene expression (Singh, et al. (2008) *Cancer Res.* 68:2961-71; Maiti, et al. (2013) *J. Immunother.* 36:112-123). An alternative non-viral approach that does not rely on transgene integration, which uses RNA electroporation, results in transient CAR expression, precluding effective T-cell persistence beyond a week (Zhao, et al. (2006) *Mol. Ther.* 13:151-159). The use of transient CAR immune cells, which require multiple injections to provide meaningful tumor responses, may reduce the destruction of normal tissues or prevent T cell accumulations to levels that increase the risk of cytokine storms (Zhao, et al. (2010) *Cancer Res.* 70:9053-61). Moreover, mRNA CAR T cells have been shown to mediate antitumor activity in patients with advanced solid tumors (Beatty, et al. (2014) *Cancer Immunology Res.* 2:112-20).

Once it is established that the transfected or transduced immune cell is capable of expressing proteins of the nucleic acid construct with the desired regulation and at a desired level, the activity of the CAR and/or anti-inflammatory or immunosuppressant protein can be determined. Subsequently, the transduced immune cells are reintroduced or administered to the subject to activate anti-inflammatory or immunosuppresive responses in the subject.

To facilitate administration, the transduced immune cells according to the invention can be made into a pharmaceutical composition or made implant-appropriate for administration in vivo, with appropriate carriers or diluents, which further can be pharmaceutically acceptable. The means of making such a composition or an implant have been described in the art (see, for instance, *Remington: The Science and Practice of Pharmacy*, Lippincott Williams & Wilkins, 21st edition (2005). Where appropriate, the transduced immune cells can be formulated into a preparation in semisolid or liquid form, such as a capsule, solution, injection, inhalant, or aerosol, in the usual ways for their respective route of administration. Means known in the art can be used to prevent or minimize release and absorption of the composition until it reaches the target tissue or organ, or to ensure timed-release of the composition. Desirably, however, a pharmaceutically acceptable form is employed which does not ineffectuate the cells of the invention. Thus, desirably the transduced immune cells can be made into a pharmaceutical composition containing a balanced salt solution, preferably Hanks' balanced salt solution, or normal saline. Additional examples of carriers or diluents include fats, oils, water, saline solutions, lipids, liposomes, resins, binders, fillers and the like, or combinations thereof. The composition may also include various antioxidants to retard oxidation of one or more component.

A pharmaceutical composition of the invention can be used alone or in combination with other well-established agents useful for treating inflammation or an autoimmune disease. Whether delivered alone or in combination with other agents, the pharmaceutical composition of the invention can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be advantageously used over inhalation for the treatment of psoriasis, vitiligo or eczema. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

Although systemic (intravenous, IV) injection is favored in clinical applications because of its ease of administration several preclinical studies (Carpenito, et al. (2009) *Proc. Natl. Acad. Sci. USA* 106:3360-3365; Song, et al. (2011) *Cancer Res.* 71:4617-4627; Parente-Pereira, et al. (2011) *J. Clin. Immunol.* 31:710-718) suggest that the regional (intratumoral, IT or intraperitoneal, IP) administration of T cells may provide optimal therapeutic effects, which may be in part due to increased T-cell trafficking. For example, it has been shown that CAR T cells remain at the site of inoculation with minimal systemic absorption when delivered via IP or IT routes (Parente-Pereira, et al. (2011) *J. Clin. Immunol.* 31:710-718). In contrast, after IV administration, CAR immune cells initially reach the lungs and then are redistributed to the spleen, liver, and lymph nodes. In addition, RNA CAR-electroporated immune cells may be particularly suitable for regional administration, due to the transient nature of the CAR expression on the immune cells (Zhao, et al. (2010) *Cancer Res.* 70:9053-9061). Furthermore, clinical studies have shown the feasibility and safety of both the intratumoral and intraperitoneal injection of immune cells (Canevari, et al. (1995) *J. Natl. Cancer Inst.* 87:1463-1469; Duval, et al. (2006) *Clin. Cancer Res.* 12:1229-123680). Overall, a local route of administration of the chimeric immune cells may provide the optimal therapeutic effect and decrease the potential for the "on-target, off-organ" toxicity discussed below.

A composition of the invention can be provided in unit dosage form wherein each dosage unit, e.g., an injection, contains a predetermined amount of the composition, alone or in appropriate combination with other active agents including conventional immunosuppressants and anti-inflammatory agents. The term unit dosage form, as used herein, refers to physically discrete units suitable as unitary dosages for human and animal subjects, each unit containing a predetermined quantity of the composition of the invention, alone or in combination with other active agents, calculated in an amount sufficient to produce the desired effect, in association with a pharmaceutically acceptable diluent, carrier, or vehicle, where appropriate. The specifications for the novel unit dosage forms of the invention depend on the particular pharmacodynamics associated with the pharmaceutical composition in the particular subject.

Desirably an effective amount or sufficient number of the isolated transduced immune cells is present in the composition and introduced into the subject such that long-term, specific, anti-inflammatory or immunosuppressive responses are established to reduce or ameliorate one or more signs or symptoms associated with inflammation or autoimmunity than would otherwise result in the absence of such treatment.

Accordingly, the amount of transduced immune cells administered should take into account the route of administration and should be such that a sufficient number of the transduced immune cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of transduced immune cells desirably should be sufficient to provide in the subject being treated at least from about $1 \times 10^6$ to about $1 \times 10^9$ transduced immune cells, even more desirably, from about $1 \times 10^7$ to about $5 \times 10^8$ transduced immune cells, although any suitable amount can be utilized either above, e.g., greater than $5 \times 10^8$ cells, or below, e.g., less than $1 \times 10^7$ cells. The dosing schedule can be based on well-established cell-based therapies (see, e.g., Topalian & Rosenberg (1987) *Acta Haematol.* 78 Suppl 1:75-6; U.S. Pat. No. 4,690,915) or an alternate continuous infusion strategy can be employed.

Any of the compositions described herein may be included in a kit. The kits will thus include, in suitable container means, cells or nucleic acid constructs or related reagents of the present invention. In some embodiments, the kit further includes an additional immunosuppressive or anti-inflammatory agent. Examples of currently available immunosuppressants and anti-inflammatory agents include, but are not limited to, cyclosporine A, cyclophosphamide, prednisone, tacrolimus (FK506), nonsteroidal anti-inflammatory agents such as aspirin, ibuprofen, diclofenac, etodolac, fenoprofen, flurbiprofen, naproxen, and oxaprozin. In certain embodiments, the additional agent may be combined with the nucleic acid construct(s) or cells of the invention or may be provided separately in the kit. In some embodiments, means of taking a sample from an individual and/or of assaying the sample may be provided in the kit. In certain embodiments the kit includes cells, buffers, cell media, vectors, primers, restriction enzymes, salts, and so forth, for example.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

The following non-limiting examples are provided to further illustrate the present invention.

Example 1: Isolation and Transduction of Treg Cells with a CAR Construct

Figure 2:
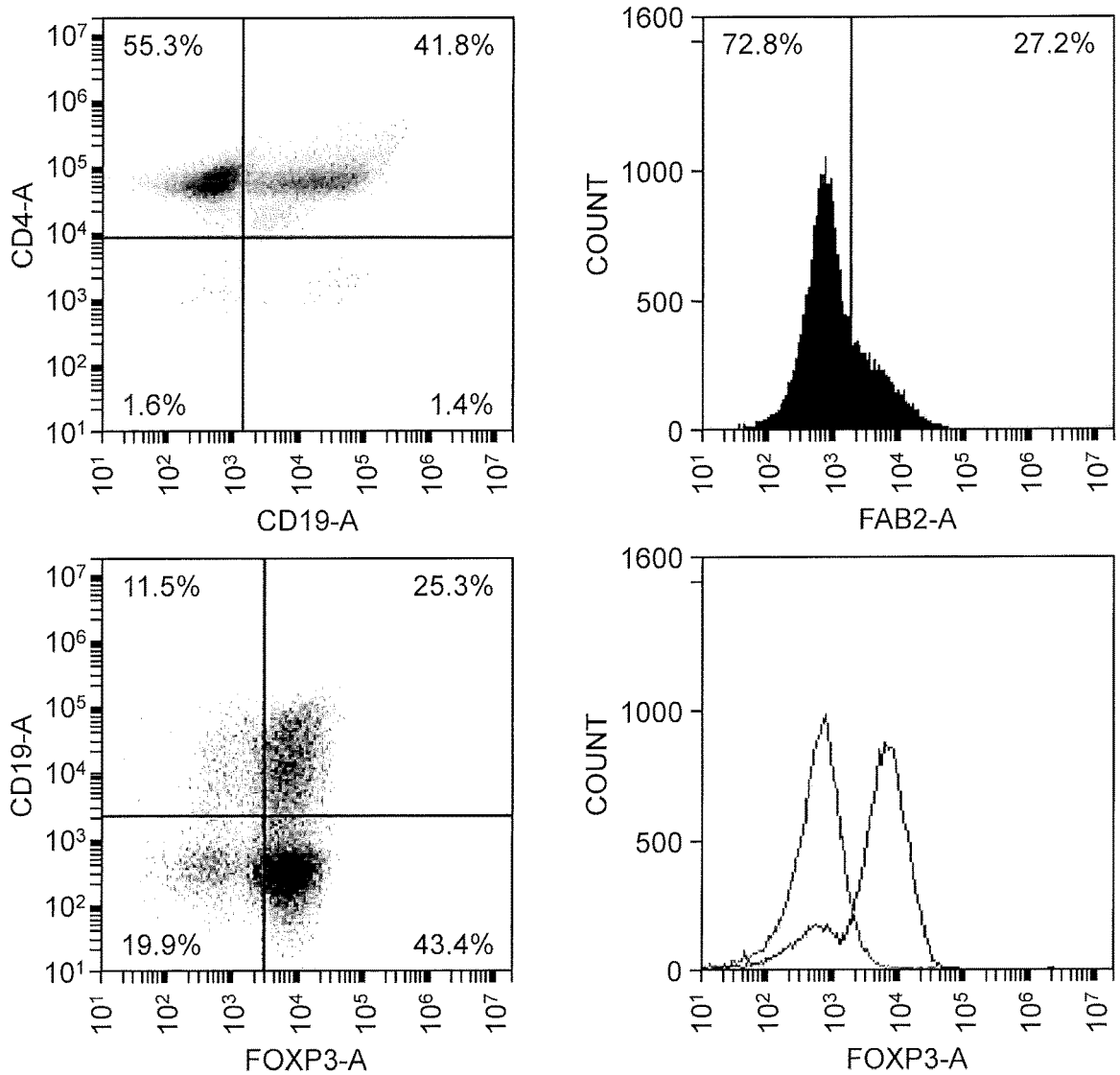
FIG. 2 shows that CD4+ CD25+ CD127− Foxp3 Treg cells can be transduced with a CAR construct without losing Foxp3 expression.

A method to isolate and expand natural T-regs was developed using commonly available magnet sort systems (Liu, et al. (2006) *J. Exp. Med.* 203:1701-11). The isolated T cells were CD4+ CD25+ CD127− Foxp3+ and had a suppressive phenotype characterized by their ability to suppress CD4+ T cell proliferation (FIG. 1). These cells were isolated, expanded, and transduced with a CAR construct composed of nucleic acids encoding a CAR protein fused to a truncated CD19 via T2A. Notably, Foxp3 expression was not lost after transduction (FIG. 2).

Example 2: Coexpression of a CAR and BCRF1

Nucleic acids encoding BCRF1 were inserted downstream of nucleic acids encoding a CAR and Foxp3 protein. Coding sequences for the CAR and Foxp3 were linked via CHYSEL peptide T2A and coding sequences for Foxp3 and BCRF1 were linked via P2A. The construct was transduced into an E86 packing cell line and BCRF1 was found to be actively secreted. ELISA analysis showed that high levels of human IL-10 were present in the E86 supernatants (~49000 pg/mL) compared to untransduced control cells (~30 pg/mL). It is expected that this construct will be viable in T cells and that BCRF1 will exert a suppressive affect on various lymphocytes.

What is claimed is:

1. A nucleic acid construct comprising (i) a nucleic acid encoding a chimeric antigen receptor comprising at least one single chain variable fragment (scFv), antigen targeting domain or recognition domain that binds a ligand at a site of inflammation or autoimmunity and (ii) a nucleic acid encoding at least one anti-inflammatory or immunosuppressant C-type lectin protein, which comprises the helminth C-type lectin protein is *Heligmosomoides polygyrus* C-type lectin-1 or *Nippostrongylus brasiliensis* C-type lectin-2.

2. The nucleic acid construct of claim 1, wherein the construct comprises a vector.

3. The nucleic acid construct of claim 1, wherein the chimeric antigen receptor further comprises at least one primary immune signaling receptor endodomain comprising an immunoreceptor tyrosine-based activation motif.

4. The nucleic acid construct of claim 3, wherein the chimeric antigen receptor further comprises at least one costimulatory endodomain.

5. The nucleic acid construct of claim 1, wherein expression of the anti-inflammatory or immunosuppressant C-type lectin protein is regulated by a promoter that is enhanced upon signaling from the chimeric antigen receptor.

6. A kit comprising the nucleic acid construct of claim 1.

7. An isolated immune cell comprising the nucleic acid construct of claim 1.

8. The isolated immune cell of claim 7, wherein the immune cell is a T lymphocyte.

9. The isolated immune cell of claim 8, wherein the T lymphocyte is a Treg cell.

10. A kit comprising one or more immune cells of claim 7.

11. A method for treating an inflammatory condition or autoimmune disease comprising delivering to a subject in need of treatment an immune cell of claim 7, thereby treating the subject's inflammation or immune-mediated autoimmunity.

12. An isolated immune cell comprising (i) a nucleic acid encoding a chimeric antigen receptor and (ii) a nucleic acid encoding at least one exogenous anti-inflammatory or immunosuppressant C-type lectin protein, which comprises the helminth C-type lectin protein is *Heligmosomoides polygyrus* C-type lectin-1 or *Nippostrongylus brasiliensis* C-type lectin-2.

13. The isolated immune cell of claim 12, wherein the chimeric antigen receptor comprises at least one scFv, antigen targeting domain or recognition domain that binds a ligand at a site of inflammation or autoimmunity.

14. The isolated immune cell of claim 12, wherein the chimeric antigen receptor further comprises:
    (a) at least one primary immune signaling receptor endodomain comprising an immunoreceptor tyrosine-based activation motif.

15. The nucleic acid construct of claim 1, further comprising an internal ribosomal entry site (IRES) or a nucleic acid which encodes a cis-acting hydrolase element (CHYSEL).

16. The nucleic acid construct of claim 15, wherein the CHYSEL encodes:
    (a) a foot and mouth disease virus (FMDV) 2A peptide;
    (b) a sea urchin (*Strongylocentrotus purpuratus*) 2A peptide;
    (c) a sponge (*Amphimedon queenslandica*) 2A peptide;
    (d) a acorn worm (*Saccoglossus kowalevskii*) 2A peptide;
    (e) an amphioxus (*Branchiostoma floridae*) 2A peptide;
    (f) a porcine teschovirus-1 2A (P2A) peptide;
    (g) a *Thosea asigna* virus 2A (T2A) peptide; or
    (h) an equine rhinitis A virus 2A (E2A) peptide.

17. The method of claim 11, wherein the inflammatory condition or autoimmune disease is any one or more of the following: rheumatoid arthritis, reactive arthritis, multiple sclerosis, Type I diabetes mellitus or autoimmune insulitis, systemic lupus erythematosus, autoimmune uveoretinitis, autoimmune vasculitis, bullous pemphigus, myasthenia gravis, autoimmune thyroiditis or Hashimoto's disease, Sjogren's syndrome, granulomatous orchitis, autoimmune oophoritis, Inflammatory bowel disease, Crohn's disease, sarcoidosis, rheumatic carditis, ankylosing spondylitis, Grave's disease, Scleroderma, Amyotrophic Lateral Sclerosis, autoimmune hemolytic anemia, psoriasis, vitiligo, eczema, primary biliary cirrhosis, autoimmune prostatitis, Goodpasture's syndrome, autoimmune hepatitis II, celiac disease, ulcerative colitis, thromboembolic syndrome, systemic vasculitides/Wegener's granulomatosis, autoimmune thrombocytopenic purpura, arthritis deformans, Lyme disease arthritis, osteoarthritis, psoriatic arthritis, gout, fibromyalgia, Still's disease, chronic uveitis, chronic back or neck pain and sciatica, Addison's disease, Gaucher's disease, Huntington's disease, muscular dystrophy, cystic fibrosis, or idiopathic pulmonary fibrosis.

18. The isolated immune cell of claim 12, wherein the immune cell is a T lymphocyte.

19. A kit comprising one or more immune cells of claim 12.

20. A method for treating an inflammatory condition or autoimmune disease comprising delivering to a subject in need of treatment an immune cell of claim 13, thereby treating the subject's inflammation or immune-mediated autoimmunity.

21. The isolated immune cell of claim 14, wherein the chimeric antigen receptor further comprises:
    (b) one or more costimulatory endodomains.

22. The nucleic acid construct of claim 16, wherein the CHYSEL encodes:
    (a) the foot and mouth disease virus (FMDV) 2A peptide comprises the amino acid sequence of SEQ ID NO: 3;
    (b) the sea urchin (*Strongylocentrotus purpuratus*) 2A peptide comprises the amino acid sequence of SEQ ID NO: 4;
    (c) the sponge (*Amphimedon queenslandica*) 2A peptide comprises the amino acid sequence of SEQ ID NO: 5 or 6;
    (d) the acorn worm (*Saccoglossus kowalevskii*) 2A peptide comprises the amino acid sequence of SEQ TD NO: 7,
    (e) the amphioxus (*Branchiostoma floridae*) 2A peptide comprises the amino acid sequence of SEQ ID NO: 8 or 9;
    (f) the porcine teschovirus-1 2A (P2A) peptide comprises the amino acid sequence of SEQ ID NO: 10;
    (g) the *Thosea asigna* virus 2A (T2A) peptide comprises the amino acid sequence of SEQ ID NO: 11; or
    (h) the equine rhinitis A virus 2A (E2A) peptide comprises the amino acid sequence of SEQ ID NO: 12.

* * * * *